US012605330B2

(12) United States Patent
    Miki et al.

(10) Patent No.: US 12,605,330 B2
(45) Date of Patent: Apr. 21, 2026

(54) SCREENING METHOD FOR OFFENSIVE ODOR-SUPPRESSING MATERIAL

(71) Applicant: Takasago International Corporation, Tokyo (JP)

(72) Inventors: Azusa Miki, Kanagawa (JP); Masato Murai, Kanagawa (JP); Ikuo Terada, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 1030 days.

(21) Appl. No.: 17/772,344

(22) PCT Filed: Oct. 30, 2020

(86) PCT No.: PCT/JP2020/040781
    § 371 (c)(1),
    (2) Date: Apr. 27, 2022

(87) PCT Pub. No.: WO2021/085590
    PCT Pub. Date: May 6, 2021

(65) Prior Publication Data
    US 2022/0411884 A1     Dec. 29, 2022

(30) Foreign Application Priority Data

Nov. 1, 2019  (JP) ................................. 2019-200172
Nov. 1, 2019  (JP) ................................. 2019-200173

(51) Int. Cl.

| | |
|---|---|
| *A61K 8/9789* | (2017.01) |
| *A23L 27/00* | (2016.01) |
| *A23L 27/20* | (2016.01) |
| *A61K 8/34* | (2006.01) |
| *A61K 8/37* | (2006.01) |
| *A61K 8/49* | (2006.01) |
| *A61Q 15/00* | (2006.01) |
| *C12N 5/16* | (2006.01) |
| *C12Q 1/6897* | (2018.01) |
| *G01N 33/566* | (2006.01) |

(52) U.S. Cl.
    CPC .......... *A61K 8/9789* (2017.08); *A23L 27/203* (2016.08); *A23L 27/84* (2016.08); *A61K 8/34* (2013.01); *A61K 8/37* (2013.01); *A61K 8/4973* (2013.01); *A61Q 15/00* (2013.01); *C12N 5/16* (2013.01); *C12Q 1/6897* (2013.01); *A23V 2002/00* (2013.01)

(58) Field of Classification Search
    None
    See application file for complete search history.

(56) References Cited

U.S. PATENT DOCUMENTS

| | | | |
|---|---|---|---|
| 10,717,945 B2 | 7/2020 | Marin et al. | |
| 2009/0123392 A1 | 5/2009 | Braun et al. | |
| 2017/0285009 A1 | 10/2017 | Rodriguez et al. | |
| 2019/0064161 A1* | 2/2019 | Pluznick ................. C12Q 1/04 |
| 2020/0345601 A1 | 11/2020 | Kao et al. | |

FOREIGN PATENT DOCUMENTS

| | | |
|---|---|---|
| CA | 3061539 A1 | 11/2018 |
| CN | 111432851 A | 7/2020 |
| JP | 11-286423 A | 10/1999 |
| JP | H11-286428 A | 10/1999 |
| JP | 2004-203839 A | 7/2004 |
| JP | 2012-050411 A | 3/2012 |
| JP | 2012-249614 A | 12/2012 |
| JP | 2014-240441 A | 12/2014 |
| JP | 6168999 B2 | 7/2017 |
| JP | 2017-153371 A | 9/2017 |
| JP | 2017-528120 A | 9/2017 |
| WO | WO-2013/115214 A1 | 8/2013 |
| WO | WO-2018/162638 A1 | 9/2018 |
| WO | WO-2019/101812 A2 | 5/2019 |
| WO | WO-2019/131789 A1 | 7/2019 |
| WO | WO-2021/085591 A1 | 5/2021 |

OTHER PUBLICATIONS

Lubran et al., "Identification of Metallic-Smelling 1-Octen-3-one and 1-Nonen-3-one from Solutions of Ferrous Sulfate," Journal of Agricultural and Food Chemistry, Sep. 16, 2005, 53(21):8325-8327.

* cited by examiner

*Primary Examiner* — Ruixiang Li
(74) *Attorney, Agent, or Firm* — Foley & Lardner LLP

(57)     ABSTRACT

The present invention relates to a screening method for materials suppressing one or more offensive odors selected from the group consisting of a 1-octen-3-one odor, a 1,5-octadien-3-one odor, a 1-octen-3-ol odor and a 1,5-octadien-3-ol odor, an offensive odor-suppressing composition for reducing the offensiveness of age-related body odors and/or underarm odors, as well as a flavor composition for reducing off-flavors derived from food and beverage products. By using the screening method of the present invention, candidate substances for materials suppressing a 1-octen-3-one odor, a 1,5-octadien-3-one odor, a 1-octen-3-ol odor and a 1,5-octadien-3-ol odor can be selected respectively from among many test substances. An offensive odor-suppressing composition comprising an active ingredient selected by using the screening method of the present invention can be expected to contribute to reduction in the offensiveness of age-related body odors and/or underarm odors and to reduction in off-flavors derived from food and beverage products.

4 Claims, 5 Drawing Sheets

Specification includes a Sequence Listing.

SEQUENCE LISTING

```
<160> NUMBER OF SEQ ID NOS: 6

<210> SEQ ID NO 1
<211> LENGTH: 1418
<212> TYPE: DNA
<213> ORGANISM: Homo sapiens
<220> FEATURE:
<221> NAME/KEY: CDS
<222> LOCATION: (53)..(991)

<400> SEQUENCE: 1
ttccagcagc ttgcgctaaa tgaattcatc aagtgactga agacaaccag tg atg gac        58
                                                          Met Asp
                                                          1 ggg gtg aat gat agc tcc ttg cag ggc ttt gtt ctg atg ggc ata tca        106
Gly Val Asn Asp Ser Ser Leu Gln Gly Phe Val Leu Met Gly Ile Ser
        5                  10                  15 gac cat ccc cag ctg gag atg atc ttt ttt ata gcc atc ctc ttc tcc        154
Asp His Pro Gln Leu Glu Met Ile Phe Phe Ile Ala Ile Leu Phe Ser
    20                  25                  30
```

-continued

```
tat ttg ctg acc cta ctt ggg aac tca acc atc atc ttg ctt tcc cgc    202
Tyr Leu Leu Thr Leu Leu Gly Asn Ser Thr Ile Ile Leu Leu Ser Arg
35              40                  45                  50 ctg gag gcc cgg ctc cat aca ccc atg tac ttc ttc ctc agc aac ctc    250
Leu Glu Ala Arg Leu His Thr Pro Met Tyr Phe Phe Leu Ser Asn Leu
                55                  60                  65 tcc tcc ttg gac ctt gct ttc gct act agt tca gtc ccc caa atg ctg    298
Ser Ser Leu Asp Leu Ala Phe Ala Thr Ser Ser Val Pro Gln Met Leu
            70                  75                  80 atc aat tta tgg gga cca ggc aag acc atc agc tat ggt ggc tgc ata    346
Ile Asn Leu Trp Gly Pro Gly Lys Thr Ile Ser Tyr Gly Gly Cys Ile
                85                  90                  95 acc cag ctc tat gtc ttc ctt tgg ctg ggg gcc acc gag tgc atc ctg    394
Thr Gln Leu Tyr Val Phe Leu Trp Leu Gly Ala Thr Glu Cys Ile Leu
        100                 105                 110 ctg gtg gtg atg gca ttt gac cgc tac gtg gca gtg tgc cgg ccc ctc    442
Leu Val Val Met Ala Phe Asp Arg Tyr Val Ala Val Cys Arg Pro Leu
115                 120                 125                 130 cgc tac acc gcc atc atg aac ccc cag ctc tgc tgg ctg ctg gct gtg    490
Arg Tyr Thr Ala Ile Met Asn Pro Gln Leu Cys Trp Leu Leu Ala Val
                135                 140                 145 att gcc tgc ctg ggt ggc ttg ggc aac tct gtg atc cag tca aca ttc    538
Ile Ala Cys Leu Gly Gly Leu Gly Asn Ser Val Ile Gln Ser Thr Phe
            150                 155                 160 act ctg cag ctc cca ttg tgt ggg cac cgg agg gtg gag gga ttc ctc    586
Thr Leu Gln Leu Pro Leu Cys Gly His Arg Arg Val Glu Gly Phe Leu
        165                 170                 175 tgc gag gtg cct gcc atg atc aaa ctg gcc tgt ggc gac aca agt ctc    634
Cys Glu Val Pro Ala Met Ile Lys Leu Ala Cys Gly Asp Thr Ser Leu
        180                 185                 190 aac cag gct gtg ctc aat ggt gtc tgc acc ttc ttc act gca gtc cca    682
Asn Gln Ala Val Leu Asn Gly Val Cys Thr Phe Phe Thr Ala Val Pro
195                 200                 205                 210 cta agc atc atc gtg atc tcc tac tgc ctc att gct cag gca gtg ctg    730
Leu Ser Ile Ile Val Ile Ser Tyr Cys Leu Ile Ala Gln Ala Val Leu
                215                 220                 225 aaa atc cgc tct gca gag ggg agg cga aag gcg ttc aat acg tgc ctc    778
Lys Ile Arg Ser Ala Glu Gly Arg Arg Lys Ala Phe Asn Thr Cys Leu
            230                 235                 240 tcc cat ctg ctg gtg gtg ttc ctc ttc tat ggc tca gcc agc tat ggg    826
Ser His Leu Leu Val Val Phe Leu Phe Tyr Gly Ser Ala Ser Tyr Gly
        245                 250                 255 tat ctg ctt ccg gcc aag aac agc aaa cag gac cag ggc aag ttc att    874
Tyr Leu Leu Pro Ala Lys Asn Ser Lys Gln Asp Gln Gly Lys Phe Ile
        260                 265                 270 tcc ctg ttc tac tcg ttg gtc aca ccc atg gtg aat ccc ctc atc tac    922
Ser Leu Phe Tyr Ser Leu Val Thr Pro Met Val Asn Pro Leu Ile Tyr
275                 280                 285                 290 acg ctg cgg aac atg gaa gtg aag ggc gca ctg agg agg ttg ctg ggg    970
Thr Leu Arg Asn Met Glu Val Lys Gly Ala Leu Arg Arg Leu Leu Gly
                295                 300                 305 aaa gga aga gaa gtt ggc tga gagaacactc cttcgttatt tattgcgtct   1021
Lys Gly Arg Glu Val Gly
                310 tcatctctac atgcgtttct cattaactct ctctggccag gtgaacatga ggaatactaa   1081 ttccggtaaa accaaggcat gttcctgaca gccctaagct gacagcccta agctgttggg   1141 aacatggtta gtgttattcg taatgttcta cacttattta ccaaaaatcc tactgtggac   1201 taccgatagc aggggagaca tgttgttgag ggctcagagg ttattgacct gtgacagacc   1261
```

```
tgtctcactg tctctgtctc tgttgcccac atgttattta atatgcctta tatttctgca          1321
gaattctgta cttttctaag caaagcacct ccacttgcag tatcttacat aatgttacta          1381
taattccata aaatcaagcc atgtattatt aacttca                                   1418
```

<210> SEQ ID NO 2
<211> LENGTH: 312
<212> TYPE: PRT
<213> ORGANISM: Homo sapiens

<400> SEQUENCE: 2

```
Met Asp Gly Val Asn Asp Ser Ser Leu Gln Gly Phe Val Leu Met Gly
1               5                   10                  15

Ile Ser Asp His Pro Gln Leu Glu Met Ile Phe Phe Ile Ala Ile Leu
                20                  25                  30

Phe Ser Tyr Leu Leu Thr Leu Leu Gly Asn Ser Thr Ile Ile Leu Leu
            35                  40                  45

Ser Arg Leu Glu Ala Arg Leu His Thr Pro Met Tyr Phe Phe Leu Ser
        50                  55                  60

Asn Leu Ser Ser Leu Asp Leu Ala Phe Ala Thr Ser Ser Val Pro Gln
65                  70                  75                  80

Met Leu Ile Asn Leu Trp Gly Pro Gly Lys Thr Ile Ser Tyr Gly Gly
                85                  90                  95

Cys Ile Thr Gln Leu Tyr Val Phe Leu Trp Leu Gly Ala Thr Glu Cys
            100                 105                 110

Ile Leu Leu Val Val Met Ala Phe Asp Arg Tyr Val Ala Val Cys Arg
        115                 120                 125

Pro Leu Arg Tyr Thr Ala Ile Met Asn Pro Gln Leu Cys Trp Leu Leu
    130                 135                 140

Ala Val Ile Ala Cys Leu Gly Gly Leu Gly Asn Ser Val Ile Gln Ser
145                 150                 155                 160

Thr Phe Thr Leu Gln Leu Pro Leu Cys Gly His Arg Arg Val Glu Gly
                165                 170                 175

Phe Leu Cys Glu Val Pro Ala Met Ile Lys Leu Ala Cys Gly Asp Thr
            180                 185                 190

Ser Leu Asn Gln Ala Val Leu Asn Gly Val Cys Thr Phe Phe Thr Ala
        195                 200                 205

Val Pro Leu Ser Ile Ile Val Ile Ser Tyr Cys Leu Ile Ala Gln Ala
    210                 215                 220

Val Leu Lys Ile Arg Ser Ala Glu Gly Arg Arg Lys Ala Phe Asn Thr
225                 230                 235                 240

Cys Leu Ser His Leu Leu Val Val Phe Leu Phe Tyr Gly Ser Ala Ser
                245                 250                 255

Tyr Gly Tyr Leu Leu Pro Ala Lys Asn Ser Lys Gln Asp Gln Gly Lys
            260                 265                 270

Phe Ile Ser Leu Phe Tyr Ser Leu Val Thr Pro Met Val Asn Pro Leu
        275                 280                 285

Ile Tyr Thr Leu Arg Asn Met Glu Val Lys Gly Ala Leu Arg Arg Leu
    290                 295                 300

Leu Gly Lys Gly Arg Glu Val Gly
305                 310
```

<210> SEQ ID NO 3
<211> LENGTH: 942
<212> TYPE: DNA

-continued

```
<213> ORGANISM: Homo sapiens
<220> FEATURE:
<221> NAME/KEY: CDS
<222> LOCATION: (1)..(942)

<400> SEQUENCE: 3 atg aaa aaa gaa caa gat tct aat gtg aca gaa ttt gtt ctt ctg ggc        48
Met Lys Lys Glu Gln Asp Ser Asn Val Thr Glu Phe Val Leu Leu Gly
1               5                   10                  15 cta tca tct tct tgg gag ctg cag cta ttt ctc ttc tta cta ttt ttg        96
Leu Ser Ser Ser Trp Glu Leu Gln Leu Phe Leu Phe Leu Leu Phe Leu
                20                  25                  30 ttt ttt tac att gct att gtc ctg gga aac ctc ttg ata gtg gta aca       144
Phe Phe Tyr Ile Ala Ile Val Leu Gly Asn Leu Leu Ile Val Val Thr
            35                  40                  45 gtg caa gcc cat gct cac ctg ctc caa tct cct atg tat tat ttt tta       192
Val Gln Ala His Ala His Leu Leu Gln Ser Pro Met Tyr Tyr Phe Leu
        50                  55                  60 ggt cat ctc tct ttc att gac cta tgc ctg agc tgt gtt act gtg cca       240
Gly His Leu Ser Phe Ile Asp Leu Cys Leu Ser Cys Val Thr Val Pro
65                  70                  75                  80 aag atg tta ggg gat ttc cta cag cag ggc aag agc atc tct ttt tca       288
Lys Met Leu Gly Asp Phe Leu Gln Gln Gly Lys Ser Ile Ser Phe Ser
                85                  90                  95 gga tgc ctg gcc cag atc tac ttc ctc cac ttt cta gga gcc agt gag       336
Gly Cys Leu Ala Gln Ile Tyr Phe Leu His Phe Leu Gly Ala Ser Glu
            100                 105                 110 atg ttt ttg ctg aca gtc atg gcc tat gac agg tat gtt gcc atc tgt       384
Met Phe Leu Leu Thr Val Met Ala Tyr Asp Arg Tyr Val Ala Ile Cys
        115                 120                 125 aac cct ttg cgc tac ctt aca gtc atg aac ccc cag cta tgc ctt tgg       432
Asn Pro Leu Arg Tyr Leu Thr Val Met Asn Pro Gln Leu Cys Leu Trp
        130                 135                 140 ttg gtt ctt gcc tgc tgg tgt ggg ggt ttt atc cac tct atc atg cag       480
Leu Val Leu Ala Cys Trp Cys Gly Gly Phe Ile His Ser Ile Met Gln
145                 150                 155                 160 gtc ata cta gtc atc cag ctg cct ttc tgt ggg ccc aat gaa ctg gac       528
Val Ile Leu Val Ile Gln Leu Pro Phe Cys Gly Pro Asn Glu Leu Asp
                165                 170                 175 aac ttc tac tgt gat gtc cca caa gtc atc aag ctg gcc tgc atg gac       576
Asn Phe Tyr Cys Asp Val Pro Gln Val Ile Lys Leu Ala Cys Met Asp
            180                 185                 190 acc tat gtg gta gag gtg ctg gtg ata gcc aac agt ggt ctg ctg tct       624
Thr Tyr Val Val Glu Val Leu Val Ile Ala Asn Ser Gly Leu Leu Ser
        195                 200                 205 ctt gtc tgc ttc ttg gtc tta cta ttc tct tat gct atc atc ctg atc       672
Leu Val Cys Phe Leu Val Leu Leu Phe Ser Tyr Ala Ile Ile Leu Ile
        210                 215                 220 acc ctg aga aca cac ttc tgc cag ggc cag aac aag gtc ttc tct acc       720
Thr Leu Arg Thr His Phe Cys Gln Gly Gln Asn Lys Val Phe Ser Thr
225                 230                 235                 240 tgt gct tct cac ctg aca gtg gtc agc ctg atc ttc gtg cca tgc gta       768
Cys Ala Ser His Leu Thr Val Val Ser Leu Ile Phe Val Pro Cys Val
                245                 250                 255 ttc atc tat ttg agg cct ttc tgc agc ttc tct gtg gat aag ata ttc       816
Phe Ile Tyr Leu Arg Pro Phe Cys Ser Phe Ser Val Asp Lys Ile Phe
            260                 265                 270 tcc ttg ttt tac aca gtg att aca cct atg ttg aac ccc ctc atc tac       864
Ser Leu Phe Tyr Thr Val Ile Thr Pro Met Leu Asn Pro Leu Ile Tyr
        275                 280                 285
```

-continued

```
aca ctc aga aat act gat atg aag aca gct atg aag aag ctg agg ata        912
Thr Leu Arg Asn Thr Asp Met Lys Thr Ala Met Lys Lys Leu Arg Ile
    290             295             300 aaa cca tgt ggc att cca ttg cct tgt taa                                942
Lys Pro Cys Gly Ile Pro Leu Pro Cys
305             310

<210> SEQ ID NO 4
<211> LENGTH: 313
<212> TYPE: PRT
<213> ORGANISM: Homo sapiens

<400> SEQUENCE: 4

Met Lys Lys Glu Gln Asp Ser Asn Val Thr Glu Phe Val Leu Leu Gly
1               5                   10                  15

Leu Ser Ser Ser Trp Glu Leu Gln Leu Phe Leu Phe Leu Leu Phe Leu
                20                  25                  30

Phe Phe Tyr Ile Ala Ile Val Leu Gly Asn Leu Leu Ile Val Val Thr
            35                  40                  45

Val Gln Ala His Ala His Leu Leu Gln Ser Pro Met Tyr Tyr Phe Leu
    50                  55                  60

Gly His Leu Ser Phe Ile Asp Leu Cys Leu Ser Cys Val Thr Val Pro
65                  70                  75                  80

Lys Met Leu Gly Asp Phe Leu Gln Gln Gly Lys Ser Ile Ser Phe Ser
                85                  90                  95

Gly Cys Leu Ala Gln Ile Tyr Phe Leu His Phe Leu Gly Ala Ser Glu
                100                 105                 110

Met Phe Leu Leu Thr Val Met Ala Tyr Asp Arg Tyr Val Ala Ile Cys
            115                 120                 125

Asn Pro Leu Arg Tyr Leu Thr Val Met Asn Pro Gln Leu Cys Leu Trp
    130                 135                 140

Leu Val Leu Ala Cys Trp Cys Gly Gly Phe Ile His Ser Ile Met Gln
145                 150                 155                 160

Val Ile Leu Val Ile Gln Leu Pro Phe Cys Gly Pro Asn Glu Leu Asp
                165                 170                 175

Asn Phe Tyr Cys Asp Val Pro Gln Val Ile Lys Leu Ala Cys Met Asp
            180                 185                 190

Thr Tyr Val Val Glu Val Leu Val Ile Ala Asn Ser Gly Leu Leu Ser
            195                 200                 205

Leu Val Cys Phe Leu Val Leu Leu Phe Ser Tyr Ala Ile Ile Leu Ile
    210                 215                 220

Thr Leu Arg Thr His Phe Cys Gln Gly Gln Asn Lys Val Phe Ser Thr
225                 230                 235                 240

Cys Ala Ser His Leu Thr Val Val Ser Leu Ile Phe Val Pro Cys Val
            245                 250                 255

Phe Ile Tyr Leu Arg Pro Phe Cys Ser Phe Ser Val Asp Lys Ile Phe
            260                 265                 270

Ser Leu Phe Tyr Thr Val Ile Thr Pro Met Leu Asn Pro Leu Ile Tyr
    275                 280                 285

Thr Leu Arg Asn Thr Asp Met Lys Thr Ala Met Lys Lys Leu Arg Ile
    290                 295                 300

Lys Pro Cys Gly Ile Pro Leu Pro Cys
305                 310

<210> SEQ ID NO 5
<211> LENGTH: 2445
```

```
<212> TYPE: DNA
<213> ORGANISM: Bos taurus
<220> FEATURE:
<221> NAME/KEY: CDS
<222> LOCATION: (1)..(1047)

<400> SEQUENCE: 5 atg aac ggg acc gag ggc cca aac ttc tac gtg cct ttc tcc aac aag      48
Met Asn Gly Thr Glu Gly Pro Asn Phe Tyr Val Pro Phe Ser Asn Lys
1               5                   10                  15 acg ggc gtg gtg cgc agc ccc ttc gag gcc ccg cag tac tac ctg gcg      96
Thr Gly Val Val Arg Ser Pro Phe Glu Ala Pro Gln Tyr Tyr Leu Ala
            20                  25                  30 gag cca tgg cag ttc tcc atg ctg gcc gcc tac atg ttc ctg ctg atc     144
Glu Pro Trp Gln Phe Ser Met Leu Ala Ala Tyr Met Phe Leu Leu Ile
        35                  40                  45 atg ctt ggc ttc ccc atc aac ttc ctc acg ctg tac gtc aca gtc cag     192
Met Leu Gly Phe Pro Ile Asn Phe Leu Thr Leu Tyr Val Thr Val Gln
    50                  55                  60 cac aag aag ctg cgc aca ccc ctc aac tac atc ctg ctc aac ctg gcc     240
His Lys Lys Leu Arg Thr Pro Leu Asn Tyr Ile Leu Leu Asn Leu Ala
65                  70                  75                  80 gtg gcc gac ctc ttc atg gtc ttc ggg ggc ttc acc acc acc ctc tac     288
Val Ala Asp Leu Phe Met Val Phe Gly Gly Phe Thr Thr Thr Leu Tyr
                85                  90                  95 acc tct ctg cac gga tac ttc gtc ttt ggg ccc acg ggc tgc aac ctg     336
Thr Ser Leu His Gly Tyr Phe Val Phe Gly Pro Thr Gly Cys Asn Leu
            100                 105                 110 gag ggc ttc ttt gcc acc ctg ggc ggt gaa att gca ctg tgg tcc ttg     384
Glu Gly Phe Phe Ala Thr Leu Gly Gly Glu Ile Ala Leu Trp Ser Leu
        115                 120                 125 gtg gtc ctg gcc atc gag cgg tac gtg gtg gtg tgc aag ccc atg agc     432
Val Val Leu Ala Ile Glu Arg Tyr Val Val Val Cys Lys Pro Met Ser
    130                 135                 140 aac ttc cgc ttc ggg gag aac cac gcc atc atg ggc gtc gcc ttc acc     480
Asn Phe Arg Phe Gly Glu Asn His Ala Ile Met Gly Val Ala Phe Thr
145                 150                 155                 160 tgg gtc atg gct ctg gcc tgt gcc gcg ccc ccc ctc gtc ggc tgg tcc     528
Trp Val Met Ala Leu Ala Cys Ala Ala Pro Pro Leu Val Gly Trp Ser
                165                 170                 175 agg tac atc ccg gag ggc atg cag tgc tcg tgc ggg att gac tac tac     576
Arg Tyr Ile Pro Glu Gly Met Gln Cys Ser Cys Gly Ile Asp Tyr Tyr
            180                 185                 190 acg ccc cac gag gag acc aac aat gag tcg ttc gtc atc tac atg ttc     624
Thr Pro His Glu Glu Thr Asn Asn Glu Ser Phe Val Ile Tyr Met Phe
        195                 200                 205 gtg gtc cac ttc atc atc ccc ctg att gtc ata ttc ttc tgc tac ggg     672
Val Val His Phe Ile Ile Pro Leu Ile Val Ile Phe Phe Cys Tyr Gly
    210                 215                 220 cag ctg gtg ttc acc gtc aag gag gcg gct gcc cag cag cag gag tcg     720
Gln Leu Val Phe Thr Val Lys Glu Ala Ala Ala Gln Gln Gln Glu Ser
225                 230                 235                 240 gcc acc act cag aag gcc gag aag gag gtc acc cgc atg gtg atc atc     768
Ala Thr Thr Gln Lys Ala Glu Lys Glu Val Thr Arg Met Val Ile Ile
                245                 250                 255 atg gtc atc gct ttc cta atc tgc tgg ctg ccc tac gct ggg gtg gcg     816
Met Val Ile Ala Phe Leu Ile Cys Trp Leu Pro Tyr Ala Gly Val Ala
            260                 265                 270 ttc tac atc ttc acc cat cag ggc tct gac ttt ggc ccc atc ttc atg     864
Phe Tyr Ile Phe Thr His Gln Gly Ser Asp Phe Gly Pro Ile Phe Met
        275                 280                 285
```

-continued

```
acc atc ccg gct ttc ttt gcc aag act tct gcc gtc tac aac ccc gtc      912
Thr Ile Pro Ala Phe Phe Ala Lys Thr Ser Ala Val Tyr Asn Pro Val
    290             295             300 atc tac atc atg atg aac aag cag ttc cgg aac tgc atg gtc acc act      960
Ile Tyr Ile Met Met Asn Lys Gln Phe Arg Asn Cys Met Val Thr Thr
305             310             315             320 ctc tgc tgt ggc aag aac ccg ctg ggt gac gac gag gcc tcc acc acc     1008
Leu Cys Cys Gly Lys Asn Pro Leu Gly Asp Asp Glu Ala Ser Thr Thr
            325             330             335 gtc tcc aag aca gag acc agc cag gtg gcg cct gcc taa gcccctccag     1057
Val Ser Lys Thr Glu Thr Ser Gln Val Ala Pro Ala
            340             345 ggactccgtg gccagctgca ggagtccctc agcccccacc ccacccccagc ctcagcagct     1117 ccatcaggag ccgcgcctgt cggaaccagc tctcacaggc tccctgagtg taaacacaaa     1177
gaccaaccaa ccaaatgcaa aagaatcaac gagagaaaca ggaggcgcct cacgtggcag     1237
gggcggcccg atctggagtc ctgatttccc gggggcccgc tgtagatcca ctcccccag     1297 ctcatctctc agctacacaa gagctcttgc tctggaaaag tgtcccagct tagggataag     1357
tgagtagcac atgacggggc atgccgtagg tgcttattaa taaatgctag gtggaggaaa     1417
gaaggaatga atggagagat gaacgggtcg ggagggcata ggcatcctct tacaacatgt     1477
tagcagcagc agcagcagct cgccttggc tcatgacctt gagcagctgt tttgtccttg     1537
ggcctcactt tcttccccca tacaatggga attccaaatc tctcctcaca cgggctgctg     1597
ggaagatcaa atgagattgt gtgtgtgtgc gtgcgtgcgt gctcgcttgt gtgagctctt     1657
tgtaaatagt aaggagctgg acagactgta gttaacatta tgaataatat caagtaatat     1717
aagtaattca tctcctatga tcatctcctc ttgatagcga ccactttgag actgggcaag     1777
gctctaagca tccagcctcg tcaggcttat aaacattaga cagatggcaa ggtcagacca     1837
gcgccgggtg gtgggccaca gggaaggacg gtcaaggaaa tgcagagtgc aggcatcagg     1897
cctgagaaga aaacaaaaac caaaaaaaca acatcagagg accagagtct ggggccagtg     1957
cagagccccc atgacgcggg ccactccctc ccagtgcaac ccccagagag acaggtcttg     2017
ctctcggcat ctgaaaaacc actagctctc ctgcccagca cccaggctgc agtatctctg     2077
ggcccgtatg gagcttctag aagttatgtt tacctgccca catttaacga agagctgggt     2137
ccccaacatc accttgtct caaaaagagc ttaaaaaaca aaagcgtggg aaatccggct     2197
ggacccacct tcccctgggg aagttcacag atcacagatt ttagctccct tgctgggcaa     2257
gccttcagcg gctccagtcc attctccact ccggagagtc cttgctgctg agaggctggc     2317
tgggactcta ggacatcaga atcgagccgc ctcataactg cccctcctcc actacataac     2377
caaagcggga agtctacct ctccccagct ctgcctggag acgaaggcaa attggggtat     2437
taaaagct                                                            2445
```

<210> SEQ ID NO 6
<211> LENGTH: 348
<212> TYPE: PRT
<213> ORGANISM: Bos taurus

<400> SEQUENCE: 6

```
Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
            20                  25                  30
```

-continued

```
Glu Pro Trp Gln Phe Ser Met Leu Ala Ala Tyr Met Phe Leu Leu Ile
    35              40              45

Met Leu Gly Phe Pro Ile Asn Phe Leu Thr Leu Tyr Val Thr Val Gln
    50              55              60

His Lys Lys Leu Arg Thr Pro Leu Asn Tyr Ile Leu Leu Asn Leu Ala
65              70              75              80

Val Ala Asp Leu Phe Met Val Phe Gly Gly Phe Thr Thr Thr Leu Tyr
            85              90              95

Thr Ser Leu His Gly Tyr Phe Val Phe Gly Pro Thr Gly Cys Asn Leu
            100             105             110

Glu Gly Phe Phe Ala Thr Leu Gly Gly Glu Ile Ala Leu Trp Ser Leu
            115             120             125

Val Val Leu Ala Ile Glu Arg Tyr Val Val Val Cys Lys Pro Met Ser
    130             135             140

Asn Phe Arg Phe Gly Glu Asn His Ala Ile Met Gly Val Ala Phe Thr
145             150             155             160

Trp Val Met Ala Leu Ala Cys Ala Ala Pro Pro Leu Val Gly Trp Ser
            165             170             175

Arg Tyr Ile Pro Glu Gly Met Gln Cys Ser Cys Gly Ile Asp Tyr Tyr
            180             185             190

Thr Pro His Glu Glu Thr Asn Asn Glu Ser Phe Val Ile Tyr Met Phe
            195             200             205

Val Val His Phe Ile Ile Pro Leu Ile Val Ile Phe Phe Cys Tyr Gly
    210             215             220

Gln Leu Val Phe Thr Val Lys Glu Ala Ala Ala Gln Gln Gln Glu Ser
225             230             235             240

Ala Thr Thr Gln Lys Ala Glu Lys Glu Val Thr Arg Met Val Ile Ile
            245             250             255

Met Val Ile Ala Phe Leu Ile Cys Trp Leu Pro Tyr Ala Gly Val Ala
            260             265             270

Phe Tyr Ile Phe Thr His Gln Gly Ser Asp Phe Gly Pro Ile Phe Met
            275             280             285

Thr Ile Pro Ala Phe Phe Ala Lys Thr Ser Ala Val Tyr Asn Pro Val
    290             295             300

Ile Tyr Ile Met Met Asn Lys Gln Phe Arg Asn Cys Met Val Thr Thr
305             310             315             320

Leu Cys Cys Gly Lys Asn Pro Leu Gly Asp Asp Glu Ala Ser Thr Thr
            325             330             335

Val Ser Lys Thr Glu Thr Ser Gln Val Ala Pro Ala
            340             345
```

SCREENING METHOD FOR OFFENSIVE ODOR-SUPPRESSING MATERIAL

CROSS-REFERENCE TO RELATED APPLICATIONS

This application is the U.S. National Stage of PCT/JP2020/040781, filed Oct. 30, 2020, which claims priority to JP 2019-200172, filed Nov. 1, 2019, and JP 2019-200173, filed Nov. 1, 2019.

The instant application contains a Sequence Listing which has been submitted in ASCII format via EFS-WEB and is hereby incorporated by reference in its entirety. Said ASCII copy, created on Apr. 26, 2022, is named sequence.txt and is 26,091 bytes.

TECHNICAL FIELD

The present invention relates to a screening method for materials suppressing one or more offensive odors selected from the group consisting of a 1-octen-3-one odor, a 1,5-octadien-3-one odor, a 1-octen-3-ol odor and a 1,5-octadien-3-ol odor, an offensive odor-suppressing composition for reducing the offensiveness of age-related body odors and/or underarm odors, as well as a flavor composition for reducing off-flavors derived from food and beverage products.

BACKGROUND ART

Ambient odors and offensive odors perceived as unpleasant in daily life are strongly desired to be eliminated more effectively for improved living environments. In recent years, there has been growing awareness of body odors, among others. Further, food and beverage products are known to produce off-odors (off-flavors) over time, which in turn reduce the quality of the food and beverage products.

Body odors are broadly divided into two categories, i.e., the "smell of each body part" (e.g., mouth odor, foot odor, underarm odor, scalp odor) and the "combined smell arising from the body trunk." The "combined smell arising from the body trunk" is known to change with age, and age-related body odors, which are observed at middle age or later, very strongly tend to be disfavored. As to substances responsible for causing such age-related body odors, unsaturated aldehydes such as trans-2-nonenal and trans-2-octenal have been reported to cause age-related body odors (Patent Literature 1). Moreover, vinyl ketones such as 1-octen-3-one and 1,5-octadien-3-one have a very low odor threshold and a strong metallic odor, and are reported to be greatly involved in underarm odors (Non-patent Literature 1). Moreover, nonenal, 1-octen-3-one, 1,5-octadien-3-one and so on are also known as off-flavors (Patent Literatures 2 and 3, Non-patent Literature 2).

Selective odor elimination techniques based on antagonistic mechanism are designed to search for olfactory receptors responding to particular odorous substances and to suppress their activation with particular substances, and the potential of these techniques is becoming clear. For example, olfactory receptor OR2W1 responds to hexanoic acid, which is among offensive odors. Substances inhibiting the activity of this OR2W1 are exemplified by florhydral, and florhydral has been reported to suppress an offensive odor induced by hexanoic acid in sensory testing (Patent Literature 4).

CITATION LIST

Patent Literature

Patent Literature 1: JP H11-286423 A
Patent Literature 2: JP 2017-153371 A
Patent Literature 3: Japanese Patent No. 6168999
Patent Literature 4: JP 2012-50411 A

Non-Patent Literature

Non-patent Literature 1: "Mechanism and Regulation of Body Malodor Generation (1)" Satoru Iida et al., J. Soc. Cosmet. Chem. Jpn. Vol. 37, No. 3 (2003)
Non-patent Literature 2: "Flavor Components in Edible Fats and Oils" Yasushi Endo, Journal of Japan Oil Chemists' Society, Vol. 48, No. 10 (1999)

SUMMARY OF INVENTION

Technical Problem

Screening may be possible for candidate substances for offensive odor-suppressing materials when olfactory receptors responding to known offensive odor-causing substances are searched and used for this purpose. However, such olfactory receptors responding to one or more offensive odor-causing substances selected from the group consisting of 1-octen-3-one, 1,5-octadien-3-one, 1-octen-3-ol and 1,5-octadien-3-ol have not been widely known so far.

Under these circumstances, there has been a desire to search for olfactory receptors responding to one or more offensive odor-causing substances selected from the group consisting of 1-octen-3-one, 1,5-octadien-3-one, 1-octen-3-ol and 1,5-octadien-3-ol, and thereby provide a screening method for materials suppressing one or more offensive odors selected from the group consisting of a 1-octen-3-one odor, a 1,5-octadien-3-one odor, a 1-octen-3-ol odor and a 1,5-octadien-3-ol odor, and also provide an offensive odor-suppressing composition for reducing the offensiveness of age-related body odors and/or underarm odors, as well as a flavor composition for reducing off-flavors derived from food and beverage products.

Solution to Problem

As a result of extensive and intensive efforts made to solve the problems stated above, the inventors of the present invention have succeeded in newly identifying olfactory receptors responding respectively to one or more offensive odor-causing substances selected from the group consisting of 1-octen-3-one, 1,5-octadien-3-one, 1-octen-3-ol and 1,5-octadien-3-ol. The inventors of the present invention have made further studies and have found that the use of these olfactory receptors enables the evaluation and selection of materials suppressing age-related body odors and/or underarm odors, and materials reducing off-flavors, as well as materials suppressing one or more offensive odors selected from the group consisting of a 1-octen-3-one odor, a 1,5-octadien-3-one odor, a 1-octen-3-ol odor and a 1,5-octadien-3-ol odor, by means of the masking effect of olfactory receptor antagonists. As a result, the inventors of the present invention have found that antagonist candidate compounds suppressing the response of these olfactory receptors including OR2C1 and OR4Q3 are excellent not only in the effect of suppressing age-related body odors and/or underarm odors, but also in the effect of reducing off-flavors derived from food and beverage products.

Namely, the present invention provides a screening method for materials suppressing one or more offensive odors selected from the group consisting of a 1-octen-3-one odor, a 1,5-octadien-3-one odor, a 1-octen-3-ol odor and a 1,5-octadien-3-ol odor, an offensive odor-suppressing composition for reducing the offensiveness of age-related body odors and/or underarm odors, as well as a flavor composition for reducing off-flavors derived from food and beverage products, as shown below.

[1] A screening method for materials suppressing one or more offensive odors selected from the group consisting of a 1-octen-3-one odor, a 1,5-octadien-3-one odor, a 1-octen-3-ol odor and a 1,5-octadien-3-ol odor, the method comprising the following steps:

adding a test substance and one or more offensive odor-causing substances selected from the group consisting of 1-octen-3-one, 1,5-octadien-3-one, 1-octen-3-ol and 1,5-octadien-3-ol to at least one olfactory receptor polypeptide selected from the group consisting of (a) OR2C1 and OR4Q3, and (b) polypeptides which comprise an amino acid sequence sharing an identity of at least 80% with the amino acid sequence of any of the polypeptides in (a) and which are responsive to one or more offensive odor-causing substances selected from the group consisting of 1-octen-3-one, 1,5-octadien-3-one, 1-octen-3-ol and 1,5-octadien-3-ol;

measuring the response of the olfactory receptor polypeptide to the one or more offensive odor-causing substances selected from the group consisting of 1-octen-3-one, 1,5-octadien-3-one, 1-octen-3-ol and 1,5-octadien-3-ol; and identifying a test substance that suppresses the response of the olfactory receptor polypeptide on the basis of the measured response.

[2] The method according to [1] above, wherein the offensive odors are a 1-octen-3-one odor and/or a 1,5-octadien-3-one odor.

[3] The method according to [1] or [2] above, wherein the response of the olfactory receptor polypeptide is measured on cells isolated from a living body expressing the olfactory receptor polypeptide or on cells genetically engineered to artificially express the olfactory receptor polypeptide.

[4] The method according to any one of [1] to [3] above, wherein the response of the olfactory receptor polypeptide is measured by reporter gene assay.

Advantageous Effects of Invention

The method of the present invention allows screening for candidate substances for materials suppressing one or more offensive odors selected from the group consisting of a 1-octen-3-one odor, a 1,5-octadien-3-one odor, a 1-octen-3-ol odor and a 1,5-octadien-3-ol odor. The screening method of the present invention can be expected to contribute to the development of materials suppressing one or more offensive odors selected from the group consisting of a 1-octen-3-one odor, a 1,5-octadien-3-one odor, a 1-octen-3-ol odor and a 1,5-octadien-3-ol odor.

Moreover, when attempting to develop new fragrance or flavor materials, there are problems of olfactory fatigue and variations among individuals if many candidate substances are evaluated for their odor by the human olfactory sense alone; and hence the proper selection of candidate substances may involve difficulties. According to the method of the present invention, such problems can be overcome or reduced.

Further, according to a preferred aspect of the present invention, when a group of antagonist candidate compounds suppressing the response of OR2C1 and/or OR4Q3 are used in combination with a group of particular compounds conventionally used as fragrances or flavorings, etc., a greater suppressive effect may be provided on offensive odors than when the group of antagonist candidate compounds are used alone.

DESCRIPTION OF EMBODIMENTS

Figure 1:
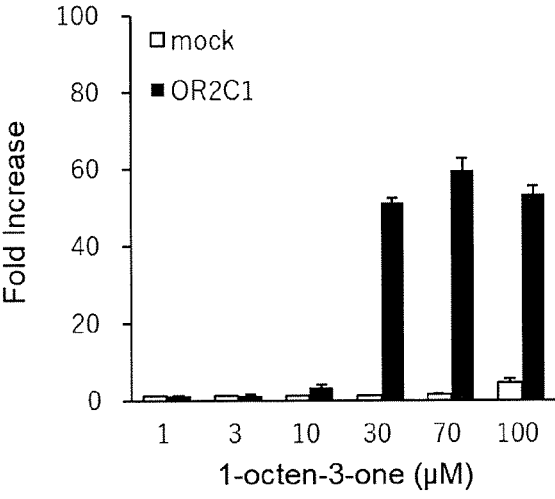
FIG. 1 shows the results measured for the response of olfactory receptor OR2C1 to 1-octen-3-one.

The screening method of the present invention, the offensive odor-suppressing composition of the present invention, as well as the flavor composition of the present invention will be described in more detail below.

1. Screening Method for 1-Octen-3-One Odor-Suppressing Materials

The screening method for 1-octen-3-one odor-suppressing materials according to the present invention is designed such that test substances are screened with olfactory receptor polypeptides responsive to 1-octen-3-one to select candidate substances for 1-octen-3-one odor-suppressing materials. This method is characterized by comprising the following steps:

adding a test substance and 1-octen-3-one to at least one olfactory receptor polypeptide selected from the group consisting of (a) OR2C1 and OR4Q3, and (b) polypeptides which comprise an amino acid sequence sharing an identity of at least 80% with the amino acid sequence of any of the polypeptides in (a) and which are responsive to 1-octen-3-one;

measuring the response of the olfactory receptor polypeptide to 1-octen-3-one; and identifying a test substance that suppresses the response of the olfactory receptor polypeptide on the basis of the measured response, i.e., identifying a test substance that suppresses the response of the olfactory receptor polypeptide on the basis of the measured response as a candidate substance for 1-octen-3-one odor-suppressing materials.

According to a preferred aspect of the present invention, the screening method for 1-octen-3-one odor-suppressing materials according to the present invention comprises the following steps:

(i) bringing an olfactory receptor polypeptide selected from the group consisting of (a) OR2C1 and OR4Q3, and (b) polypeptides which comprise an amino acid sequence sharing an identity of 80% or more with the amino acid sequence of any of the polypeptides in (a) and which are responsive to 1-octen-3-one into contact with 1-octen-3-one to measure the response of the olfactory receptor polypeptide to 1-octen-3-one;

(ii) mixing a test substance with 1-octen-3-one to measure the response of the olfactory receptor polypeptide used in step (i); and (iii) comparing the results measured in steps (i) and (ii) to select a test substance causing a reduction in the response as a candidate substance for 1-octen-3-one odor-suppressing materials.

The screening method for 1-octen-3-one odor-suppressing materials according to the present invention is configured such that candidate substances for 1-octen-3-one odor-suppressing materials are selected from among test substances on the basis of the responsiveness of each test substance to an olfactory receptor polypeptide selected from the group consisting of OR2C1, OR4Q3, and polypeptides which comprise amino acid sequences sharing an identity of 80% or more with the amino acid sequences of these polypeptides and which are responsive to offensive odor-causing substances.

In the screening method for 1-octen-3-one odor-suppressing materials according to the present invention, the term "test substance" is not limited in any way, but it refers to a subject to be tested for its suppressive effect on a 1-octen-3-one odor and is intended to mean a compound, a composition or a mixture. Likewise, the term "1-octen-3-one odor-suppressing material" is not limited in any way, but it is intended to mean a compound, a composition or a mixture, which is capable of suppressing a 1-octen-3-one odor. Moreover, the term "1-octen-3-one odor" is intended to mean an odor originating from 1-octen-3-one, as exemplified by a mushroom odor, an iron rust odor, an underarm odor, off-flavors, etc. An explanation will be given below of each step.

<Step (i)>

In step (i), an olfactory receptor polypeptide selected from the group consisting of OR2C1, OR4Q3, and polypeptides which comprise an amino acid sequence sharing an identity of 80% or more with the amino acid sequence of any of these polypeptides and which are responsive to 1-octen-3-one is brought into contact with 1-octen-3-one to measure the response of the olfactory receptor polypeptide to 1-octen-3-one.

The olfactory receptor polypeptide to be used for this purpose is an olfactory receptor polypeptide selected from the group consisting of OR2C1, OR4Q3, and polypeptides which comprise an amino acid sequence sharing an identity of 80% or more with the amino acid sequence of any of these polypeptides and which are responsive to 1-octen-3-one.

OR2C1 has been registered in GenBank under NM_012368, and is a polypeptide consisting of an amino acid sequence (SEQ ID NO: 2) encoded by DNA at positions 53 to 991 of the nucleotide sequence shown in SEQ ID NO: 1.

OR4Q3 has been registered in GenBank under NM_172194, and is a polypeptide consisting of an amino acid sequence (SEQ ID NO: 4) encoded by DNA having the nucleotide sequence shown in SEQ ID NO: 3.

Since these polypeptides strongly and selectively respond to 1-octen-3-one, the screening method using OR2C1 and/or OR4Q3 can be expected to contribute to the development of 1-octen-3-one odor-suppressing materials.

As an olfactory receptor, it is also possible to use an olfactory receptor polypeptide selected from the group consisting of polypeptides which comprise an amino acid sequence sharing an identity of 80% or more, preferably 85% or more, more preferably 90% or more, even more preferably 95% or more, and particularly preferably 98% or more with the amino acid sequence possessed by any of these polypeptides (i.e., SEQ ID NO: 2 or 4) and which are responsive to 1-octen-3-one.

Such olfactory receptor polypeptides may be used alone, or two or more of them may be used in combination.

In the present invention, there is no particular limitation on how to contact an olfactory receptor polypeptide with 1-octen-3-one to measure the response of the olfactory receptor polypeptide to 1-octen-3-one. For example, the response of the olfactory receptor polypeptide may be measured by being contacted with 1-octen-3-one on cells isolated from a living body expressing the olfactory receptor polypeptide, or alternatively, the response of the olfactory receptor polypeptide may be measured by being contacted with 1-octen-3-one on cells genetically engineered to artificially express the olfactory receptor polypeptide. The time required to contact the olfactory receptor polypeptide with 1-octen-3-one is not determined exactly because it also depends on the concentration of 1-octen-3-one and the method used for measurement. However, the response may be measured immediately after their contact, and the time required for their contact is usually 0 to 4 hours, and preferably 2 to 4 hours. The same goes for when the olfactory receptor polypeptide is contacted with 1-octen-3-one in admixture with a test substance.

Cells genetically engineered to artificially express the olfactory receptor polypeptide may be prepared when cells are transformed with a vector carrying a gene encoding the olfactory receptor polypeptide.

In a preferred aspect of the present invention, the N-terminal 20 amino acid residues of bovine rhodopsin may be integrated together with the olfactory receptor polypeptide. Upon integration of the N-terminal 20 amino acid residues of bovine rhodopsin, cell membrane expression of the olfactory receptor polypeptide may be facilitated.

Bovine rhodopsin has been registered in GenBank under NM_001014890. Bovine rhodopsin is a polypeptide consisting of an amino acid sequence (SEQ ID NO: 6) encoded by DNA at positions 1 to 1047 of the nucleotide sequence shown in SEQ ID NO: 5.

Moreover, instead of bovine rhodopsin, it is also possible to use a polypeptide which comprises an amino acid sequence sharing an identity of 80% or more, preferably 85% or more, more preferably 90% or more, even more preferably 95% or more, and particularly preferably 98% or more with the amino acid sequence shown in SEQ ID NO: 6 and which is capable of facilitating cell membrane expression of the olfactory receptor polypeptide.

It should be noted that amino acid residues of not only bovine rhodopsin but also any other polypeptides may be used as long as they can facilitate cell membrane expression of the olfactory receptor polypeptide.

There is no particular limitation on how to measure the response of the olfactory receptor polypeptide, and any technique used in the art may be used for this purpose. For example, it is known that once an odorous compound has bound to an olfactory receptor polypeptide, G protein in cells will be activated and this G protein will in turn activate adenylate cyclase to convert ATP into cyclic AMP (cAMP), thereby increasing the intracellular level of cAMP. Thus, the response of the olfactory receptor polypeptide can be measured when the level of cAMP is measured. The level of cAMP may be measured using ELISA techniques, reporter gene assay techniques, etc. Above all, it is preferred that the response of the olfactory receptor polypeptide is measured by reporter gene assay techniques using a luminophore (e.g., luciferase).

According to one embodiment of the present invention, the response of the olfactory receptor polypeptide may be evaluated on the basis of the fold increase value determined by dividing the results measured in the presence of 1-octen-3-one by the results measured in the absence of 1-octen-3-one. For example, when the response of the olfactory receptor polypeptide is measured by reporter gene assay techniques using a luminophore (e.g., luciferase), evaluation can be made using 1-octen-3-one at a concentration which gives a fold increase value of preferably 2 or more, more preferably 4 or more, and even more preferably 10 or more.

<Step (ii)>

In step (ii), a test substance is mixed with 1-octen-3-one to measure the response of the olfactory receptor used in step (i).

The response of the olfactory receptor polypeptide may be measured in the same manner as shown in step (i), except that 1-octen-3-one is mixed with the test substance and contacted with the olfactory receptor polypeptide. For example, the response of the olfactory receptor polypeptide may be measured on cells isolated from a living body expressing the olfactory receptor polypeptide, or alternatively, the response of the olfactory receptor polypeptide may be measured on cells genetically engineered to artificially express the olfactory receptor polypeptide. For proper comparison of the results measured in steps (i) and (ii), the measurement conditions in steps (i) and (ii) are preferably the same, except for the presence or absence of the test substance.

<Step (iii)>

In step (iii), the results measured in steps (i) and (ii) are compared with each other to select a test substance causing a reduction in the response as a candidate substance for 1-octen-3-one odor-suppressing materials.

In the present invention, when a reduction in the response is observed as a result of comparing the results measured in steps (i) and (ii), the test substance used in step (ii) can be evaluated as a candidate substance for 1-octen-3-one odor-suppressing materials.

In such a way as described above, test substances can be screened to select candidate substances for 1-octen-3-one odor-suppressing materials. According to the present invention, it is possible to select candidate substances for 1-octen-3-one odor-suppressing materials from among many test substances, without causing any problems such as olfactory fatigue and variations among individuals associated with sensory testing by means of the human olfactory sense.

The selected substances can be used as candidate substances for 1-octen-3-one odor-suppressing materials. If necessary, the selected substances may be subjected to modifications or the like to thereby develop novel compounds having the most suitable scent. Further, the selected substances may be blended with other fragrance or flavor materials to thereby develop fragrance or flavor materials capable of suppressing the 1-octen-3-one odor and also having the most suitable scent. The screening method of the present invention can be used to contribute to the development of new fragrance or flavor materials serving as 1-octen-3-one odor-suppressing materials.

2. Screening Method for 1,5-Octadien-3-One Odor-Suppressing Materials

The screening method for 1,5-octadien-3-one odor-suppressing materials according to the present invention is designed such that test substances are screened with olfactory receptor polypeptides responsive to 1,5-octadien-3-one to select candidate substances for 1,5-octadien-3-one odor-suppressing materials. This method is characterized by comprising the following steps:

adding a test substance and 1,5-octadien-3-one to at least one olfactory receptor polypeptide selected from the group consisting of (a) OR2C1 and OR4Q3, and (b) polypeptides which comprise an amino acid sequence sharing an identity of at least 80% with the amino acid sequence of any of the polypeptides in (a) and which are responsive to 1,5-octadien-3-one;

measuring the response of the olfactory receptor polypeptide to 1,5-octadien-3-one; and identifying a test substance that suppresses the response of the olfactory receptor polypeptide on the basis of the measured response, i.e., identifying a test substance that suppresses the response of the olfactory receptor polypeptide on the basis of the measured response as a candidate substance for 1,5-octadien-3-one odor-suppressing materials.

According to a preferred aspect of the present invention, the screening method for 1,5-octadien-3-one odor-suppressing materials according to the present invention comprises the following steps:

(i) bringing an olfactory receptor polypeptide selected from the group consisting of (a) OR2C1 and OR4Q3, and (b) polypeptides which comprise an amino acid sequence sharing an identity of 80% or more with the amino acid sequence of any of the polypeptides in (a) and which are responsive to 1,5-octadien-3-one into contact with 1,5-octadien-3-one to measure the response of the olfactory receptor polypeptide to 1,5-octadien-3-one;

(ii) mixing a test substance with 1,5-octadien-3-one to measure the response of the olfactory receptor polypeptide used in step (i); and (iii) comparing the results measured in steps (i) and (ii) to select a test substance causing a reduction in the response as a candidate substance for 1,5-octadien-3-one odor-suppressing materials.

The screening method for 1,5-octadien-3-one odor-suppressing materials according to the present invention is configured such that candidate substances for 1,5-octadien-3-one odor-suppressing materials are selected from among test substances on the basis of the responsiveness of each test substance to an olfactory receptor polypeptide selected from the group consisting of OR2C1, OR4Q3, and polypeptides which comprise amino acid sequences sharing an identity of 80% or more with the amino acid sequences of these polypeptides and which are responsive to offensive odor-causing substances.

In the screening method for 1,5-octadien-3-one odor-suppressing materials according to the present invention, the term "test substance" is not limited in any way, but it refers to a subject to be tested for its suppressive effect on a 1,5-octadien-3-one odor and is intended to mean a compound, a composition or a mixture. Likewise, the term "1,5-octadien-3-one odor-suppressing material" is not limited in any way, but it is intended to mean a compound, a composition or a mixture, which is capable of suppressing a 1,5-octadien-3-one odor. Moreover, the term "1,5-octadien-3-one odor" is intended to mean an odor originating from 1,5-octadien-3-one, as exemplified by a mushroom odor, an iron rust odor, an underarm odor, off-flavors, etc. An explanation will be given below of each step.

<Step (i)>

In step (i), an olfactory receptor polypeptide selected from the group consisting of OR2C1, OR4Q3, and polypeptides which comprise an amino acid sequence sharing an identity of 80% or more with the amino acid sequence of any of these polypeptides and which are responsive to 1,5-octadien-3-one is brought into contact with 1,5-octadien-3-one to measure the response of the olfactory receptor polypeptide to 1,5-octadien-3-one.

The olfactory receptor polypeptide to be used for this purpose is an olfactory receptor polypeptide selected from the group consisting of OR2C1, OR4Q3, and polypeptides which comprise an amino acid sequence sharing an identity of 80% or more with the amino acid sequence of any of these polypeptides and which are responsive to 1,5-octadien-3-one.

OR2C1 has been registered in GenBank under NM_012368, and is a polypeptide consisting of an amino acid sequence (SEQ ID NO: 2) encoded by DNA at positions 53 to 991 of the nucleotide sequence shown in SEQ ID NO: 1.

OR4Q3 has been registered in GenBank under NM_172194, and is a polypeptide consisting of an amino acid sequence (SEQ ID NO: 4) encoded by DNA having the nucleotide sequence shown in SEQ ID NO: 3.

Since these polypeptides strongly and selectively respond to 1,5-octadien-3-one, the screening method using OR2C1 and/or OR4Q3 can be expected to contribute to the development of 1,5-octadien-3-one odor-suppressing materials.

As an olfactory receptor, it is also possible to use an olfactory receptor polypeptide selected from the group consisting of polypeptides which comprise an amino acid sequence sharing an identity of 80% or more, preferably 85% or more, more preferably 90% or more, even more preferably 95% or more, and particularly preferably 98% or more with the amino acid sequence possessed by any of these polypeptides (i.e., SEQ ID NO: 2 or 4) and which are responsive to 1,5-octadien-3-one.

Such olfactory receptor polypeptides may be used alone, or two or more of them may be used in combination.

In the present invention, there is no particular limitation on how to contact an olfactory receptor polypeptide with 1,5-octadien-3-one to measure the response of the olfactory receptor polypeptide to 1,5-octadien-3-one. For example, the response of the olfactory receptor polypeptide may be measured by being contacted with 1,5-octadien-3-one on cells isolated from a living body expressing the olfactory receptor polypeptide, or alternatively, the response of the olfactory receptor polypeptide may be measured by being contacted with 1,5-octadien-3-one on cells genetically engineered to artificially express the olfactory receptor polypeptide. The time required to contact the olfactory receptor polypeptide with 1,5-octadien-3-one is not determined exactly because it also depends on the concentration of 1,5-octadien-3-one and the method used for measurement. However, the response may be measured immediately after their contact, and the time required for their contact is usually 0 to 4 hours, and preferably 2 to 4 hours. The same goes for when the olfactory receptor polypeptide is contacted with 1,5-octadien-3-one in admixture with a test substance.

Cells genetically engineered to artificially express the olfactory receptor polypeptide may be prepared when cells are transformed with a vector carrying a gene encoding the olfactory receptor polypeptide.

In a preferred aspect of the present invention, the N-terminal 20 amino acid residues of bovine rhodopsin may be integrated together with the olfactory receptor polypeptide. Upon integration of the N-terminal 20 amino acid residues of bovine rhodopsin, cell membrane expression of the olfactory receptor polypeptide may be facilitated.

Bovine rhodopsin has been registered in GenBank under NM_001014890. Bovine rhodopsin is a polypeptide consisting of an amino acid sequence (SEQ ID NO: 6) encoded by DNA at positions 1 to 1047 of the nucleotide sequence shown in SEQ ID NO: 5.

Moreover, instead of bovine rhodopsin, it is also possible to use a polypeptide which comprises an amino acid sequence sharing an identity of 80% or more, preferably 85% or more, more preferably 90% or more, even more preferably 95% or more, and particularly preferably 98% or more with the amino acid sequence shown in SEQ ID NO: 6 and which is capable of facilitating cell membrane expression of the olfactory receptor polypeptide.

It should be noted that amino acid residues of not only bovine rhodopsin but also any other polypeptides may be used as long as they can facilitate cell membrane expression of the olfactory receptor polypeptide.

There is no particular limitation on how to measure the response of the olfactory receptor polypeptide, and any technique used in the art may be used for this purpose. For example, it is known that once an odorous compound has bound to an olfactory receptor polypeptide, G protein in cells will be activated and this G protein will in turn activate adenylate cyclase to convert ATP into cyclic AMP (cAMP), thereby increasing the intracellular level of cAMP. Thus, the response of the olfactory receptor polypeptide can be measured when the level of cAMP is measured. The level of cAMP may be measured using ELISA techniques, reporter gene assay techniques, etc. Above all, it is preferred that the response of the olfactory receptor polypeptide is measured by reporter gene assay techniques using a luminophore (e.g., luciferase).

According to one embodiment of the present invention, the response of the olfactory receptor polypeptide may be evaluated on the basis of the fold increase value determined by dividing the results measured in the presence of 1,5-octadien-3-one by the results measured in the absence of 1,5-octadien-3-one. For example, when the response of the olfactory receptor polypeptide is measured by reporter gene assay techniques using a luminophore (e.g., luciferase), evaluation can be made using 1,5-octadien-3-one at a concentration which gives a fold increase value of preferably 2 or more, more preferably 4 or more, and even more preferably 10 or more.

<Step (ii)>

In step (ii), a test substance is mixed with 1,5-octadien-3-one to measure the response of the olfactory receptor used in step (i).

The response of the olfactory receptor polypeptide may be measured in the same manner as shown in step (i), except that 1,5-octadien-3-one is mixed with the test substance and contacted with the olfactory receptor polypeptide. For example, the response of the olfactory receptor polypeptide may be measured on cells isolated from a living body expressing the olfactory receptor polypeptide, or alternatively, the response of the olfactory receptor polypeptide may be measured on cells genetically engineered to artificially express the olfactory receptor polypeptide. For proper comparison of the results measured in steps (i) and (ii), the measurement conditions in steps (i) and (ii) are preferably the same, except for the presence or absence of the test substance.

<Step (iii)>

In step (iii), the results measured in steps (i) and (ii) are compared with each other to select a test substance causing a reduction in the response as a candidate substance for 1,5-octadien-3-one odor-suppressing materials.

In the present invention, when a reduction in the response is observed as a result of comparing the results measured in steps (i) and (ii), the test substance used in step (ii) can be evaluated as a candidate substance for 1,5-octadien-3-one odor-suppressing materials.

In such a way as described above, test substances can be screened to select candidate substances for 1,5-octadien-3-one odor-suppressing materials. According to the present invention, it is possible to select candidate substances for 1,5-octadien-3-one odor-suppressing materials from among many test substances, without causing any problems such as olfactory fatigue and variations among individuals associated with sensory testing by means of the human olfactory sense.

The selected substances can be used as candidate substances for 1,5-octadien-3-one odor-suppressing materials. If necessary, the selected substances may be subjected to modifications or the like to thereby develop novel compounds having the most suitable scent. Further, the selected substances may be blended with other fragrance or flavor materials to thereby develop fragrance or flavor materials capable of suppressing the 1,5-octadien-3-one odor and also having the most suitable scent. The screening method of the present invention can be used to contribute to the development of new fragrance or flavor materials serving as 1,5-octadien-3-one odor-suppressing materials.

3. Screening Method for 1-Octen-3-ol Odor-Suppressing Materials

The screening method for 1-octen-3-ol odor-suppressing materials according to the present invention is designed such that test substances are screened with olfactory receptor polypeptides responsive to 1-octen-3-ol to select candidate substances for 1-octen-3-ol odor-suppressing materials. This method is characterized by comprising the following steps:

adding a test substance and 1-octen-3-ol to at least one olfactory receptor polypeptide selected from the group consisting of (a) OR2C1 and OR4Q3, and (b) polypeptides which comprise an amino acid sequence sharing an identity of at least 80% with the amino acid sequence of any of the polypeptides in (a) and which are responsive to 1-octen-3-ol;

measuring the response of the olfactory receptor polypeptide to 1-octen-3-ol; and identifying a test substance that suppresses the response of the olfactory receptor polypeptide on the basis of the measured response, i.e., identifying a test substance that suppresses the response of the olfactory receptor polypeptide on the basis of the measured response as a candidate substance for 1-octen-3-ol odor-suppressing materials.

According to a preferred aspect of the present invention, the screening method for 1-octen-3-ol odor-suppressing materials according to the present invention comprises the following steps:

(i) bringing an olfactory receptor polypeptide selected from the group consisting of (a) OR2C1 and OR4Q3, and (b) polypeptides which comprise an amino acid sequence sharing an identity of 80% or more with the amino acid sequence of any of the polypeptides in (a) and which are responsive to 1-octen-3-ol into contact with 1-octen-3-ol to measure the response of the olfactory receptor polypeptide to 1-octen-3-ol;

(ii) mixing a test substance with 1-octen-3-ol to measure the response of the olfactory receptor polypeptide used in step (i); and (iii) comparing the results measured in steps (i) and (ii) to select a test substance causing a reduction in the response as a candidate substance for 1-octen-3-ol odor-suppressing materials.

The screening method for 1-octen-3-ol odor-suppressing materials according to the present invention is configured such that candidate substances for 1-octen-3-ol odor-suppressing materials are selected from among test substances on the basis of the responsiveness of each test substance to an olfactory receptor polypeptide selected from the group consisting of OR2C1, OR4Q3, and polypeptides which comprise amino acid sequences sharing an identity of 80% or more with the amino acid sequences of these polypeptides and which are responsive to offensive odor-causing substances.

In the screening method for 1-octen-3-ol odor-suppressing materials according to the present invention, the term "test substance" is not limited in any way, but it refers to a subject to be tested for its suppressive effect on a 1-octen-3-ol odor and is intended to mean a compound, a composition or a mixture. Likewise, the term "1-octen-3-ol odor-suppressing material" is not limited in any way, but it is intended to mean a compound, a composition or a mixture, which is capable of suppressing a 1-octen-3-ol odor. Moreover, the term "1-octen-3-ol odor" is intended to mean an odor originating from 1-octen-3-ol, as exemplified by a mushroom odor, an iron rust odor, an underarm odor, off-flavors, etc. An explanation will be given below of each step.

<Step (i)>

In step (i), an olfactory receptor polypeptide selected from the group consisting of OR2C1, OR4Q3, and polypeptides which comprise an amino acid sequence sharing an identity of 80% or more with the amino acid sequence of any of these polypeptides and which are responsive to 1-octen-3-ol is brought into contact with 1-octen-3-ol to measure the response of the olfactory receptor polypeptide to 1-octen-3-ol.

The olfactory receptor polypeptide to be used for this purpose is an olfactory receptor polypeptide selected from the group consisting of OR2C1, OR4Q3, and polypeptides which comprise an amino acid sequence sharing an identity of 80% or more with the amino acid sequence of any of these polypeptides and which are responsive to 1-octen-3-ol.

OR2C1 has been registered in GenBank under NM_012368, and is a polypeptide consisting of an amino acid sequence (SEQ ID NO: 2) encoded by DNA at positions 53 to 991 of the nucleotide sequence shown in SEQ ID NO: 1.

OR4Q3 has been registered in GenBank under NM_172194, and is a polypeptide consisting of an amino acid sequence (SEQ ID NO: 4) encoded by DNA having the nucleotide sequence shown in SEQ ID NO: 3.

Since these polypeptides strongly and selectively respond to 1-octen-3-ol, the screening method using OR2C1 and/or OR4Q3 can be expected to contribute to the development of 1-octen-3-ol odor-suppressing materials.

As an olfactory receptor, it is also possible to use an olfactory receptor polypeptide selected from the group consisting of polypeptides which comprise an amino acid sequence sharing an identity of 80% or more, preferably 85% or more, more preferably 90% or more, even more preferably 95% or more, and particularly preferably 98% or more with the amino acid sequence possessed by any of these polypeptides (i.e., SEQ ID NO: 2 or 4) and which are responsive to 1-octen-3-ol.

Such olfactory receptor polypeptides may be used alone, or two or more of them may be used in combination.

In the present invention, there is no particular limitation on how to contact an olfactory receptor polypeptide with 1-octen-3-ol to measure the response of the olfactory receptor polypeptide to 1-octen-3-ol. For example, the response of the olfactory receptor polypeptide may be measured by being contacted with 1-octen-3-ol on cells isolated from a living body expressing the olfactory receptor polypeptide, or alternatively, the response of the olfactory receptor polypeptide may be measured by being contacted with 1-octen-3-ol on cells genetically engineered to artificially express the olfactory receptor polypeptide. The time required to contact the olfactory receptor polypeptide with 1-octen-3-ol is not determined exactly because it also depends on the concentration of 1-octen-3-ol and the method used for measurement. However, the response may be measured immediately after their contact, and the time required for their contact is usually 0 to 4 hours, and preferably 2 to 4 hours. The same goes for when the olfactory receptor polypeptide is contacted with 1-octen-3-ol in admixture with a test substance.

Cells genetically engineered to artificially express the olfactory receptor polypeptide may be prepared when cells are transformed with a vector carrying a gene encoding the olfactory receptor polypeptide.

In a preferred aspect of the present invention, the N-terminal 20 amino acid residues of bovine rhodopsin may be integrated together with the olfactory receptor polypeptide. Upon integration of the N-terminal 20 amino acid residues of bovine rhodopsin, cell membrane expression of the olfactory receptor polypeptide may be facilitated.

Bovine rhodopsin has been registered in GenBank under NM_001014890. Bovine rhodopsin is a polypeptide consisting of an amino acid sequence (SEQ ID NO: 6) encoded by DNA at positions 1 to 1047 of the nucleotide sequence shown in SEQ ID NO: 5.

Moreover, instead of bovine rhodopsin, it is also possible to use a polypeptide which comprises an amino acid sequence sharing an identity of 80% or more, preferably 85% or more, more preferably 90% or more, even more preferably 95% or more, and particularly preferably 98% or more with the amino acid sequence shown in SEQ ID NO: 6 and which is capable of facilitating cell membrane expression of the olfactory receptor polypeptide.

It should be noted that amino acid residues of not only bovine rhodopsin but also any other polypeptides may be used as long as they can facilitate cell membrane expression of the olfactory receptor polypeptide.

There is no particular limitation on how to measure the response of the olfactory receptor polypeptide, and any technique used in the art may be used for this purpose. For example, it is known that once an odorous compound has bound to an olfactory receptor polypeptide, G protein in cells will be activated and this G protein will in turn activate adenylate cyclase to convert ATP into cyclic AMP (cAMP), thereby increasing the intracellular level of cAMP. Thus, the response of the olfactory receptor polypeptide can be measured when the level of cAMP is measured. The level of cAMP may be measured using ELISA techniques, reporter gene assay techniques, etc. Above all, it is preferred that the response of the olfactory receptor polypeptide is measured by reporter gene assay techniques using a luminophore (e.g., luciferase).

According to one embodiment of the present invention, the response of the olfactory receptor polypeptide may be evaluated on the basis of the fold increase value determined by dividing the results measured in the presence of 1-octen-3-ol by the results measured in the absence of 1-octen-3-ol. For example, when the response of the olfactory receptor polypeptide is measured by reporter gene assay techniques using a luminophore (e.g., luciferase), evaluation can be made using 1-octen-3-ol at a concentration which gives a fold increase value of preferably 2 or more, more preferably 4 or more, and even more preferably 10 or more.

<Step (ii)>

In step (ii), a test substance is mixed with 1-octen-3-ol to measure the response of the olfactory receptor used in step (i).

The response of the olfactory receptor polypeptide may be measured in the same manner as shown in step (i), except that 1-octen-3-ol is mixed with the test substance and contacted with the olfactory receptor polypeptide. For example, the response of the olfactory receptor polypeptide may be measured on cells isolated from a living body expressing the olfactory receptor polypeptide, or alternatively, the response of the olfactory receptor polypeptide may be measured on cells genetically engineered to artificially express the olfactory receptor polypeptide. For proper comparison of the results measured in steps (i) and (ii), the measurement conditions in steps (i) and (ii) are preferably the same, except for the presence or absence of the test substance.

<Step (iii)>

In step (iii), the results measured in steps (i) and (ii) are compared with each other to select a test substance causing a reduction in the response as a candidate substance for 1-octen-3-ol odor-suppressing materials.

In the present invention, when a reduction in the response is observed as a result of comparing the results measured in steps (i) and (ii), the test substance used in step (ii) can be evaluated as a candidate substance for 1-octen-3-ol odor-suppressing materials.

In such a way as described above, test substances can be screened to select candidate substances for 1-octen-3-ol odor-suppressing materials. According to the present invention, it is possible to select candidate substances for 1-octen-3-ol odor-suppressing materials from among many test substances, without causing any problems such as olfactory fatigue and variations among individuals associated with sensory testing by means of the human olfactory sense.

The selected substances can be used as candidate substances for 1-octen-3-ol odor-suppressing materials. If necessary, the selected substances may be subjected to modifications or the like to thereby develop novel compounds having the most suitable scent. Further, the selected substances may be blended with other fragrance or flavor materials to thereby develop fragrance or flavor materials capable of suppressing the 1-octen-3-ol odor and also having the most suitable scent. The screening method of the present invention can be used to contribute to the development of new fragrance or flavor materials serving as 1-octen-3-ol odor-suppressing materials.

4. Screening Method for 1,5-Octadien-3-ol Odor-Suppressing Materials

The screening method for 1,5-octadien-3-ol odor-suppressing materials according to the present invention is designed such that test substances are screened with olfactory receptor polypeptides responsive to 1,5-octadien-3-ol to select candidate substances for 1,5-octadien-3-ol odor-suppressing materials. This method is characterized by comprising the following steps:

adding a test substance and 1,5-octadien-3-ol to at least one olfactory receptor polypeptide selected from the group consisting of (a) OR2C1 and OR4Q3, and (b) polypeptides which comprise an amino acid sequence sharing an identity of at least 80% with the amino acid sequence of any of the polypeptides in (a) and which are responsive to 1,5-octadien-3-ol;

measuring the response of the olfactory receptor polypeptide to 1,5-octadien-3-ol; and identifying a test substance that suppresses the response of the olfactory receptor polypeptide on the basis of the measured response, i.e., identifying a test substance that suppresses the response of the olfactory receptor polypeptide on the basis of the measured response as a candidate substance for 1,5-octadien-3-ol odor-suppressing materials.

According to a preferred aspect of the present invention, the screening method for 1,5-octadien-3-ol odor-suppressing materials according to the present invention comprises the following steps:

(i) bringing an olfactory receptor polypeptide selected from the group consisting of (a) OR2C1 and OR4Q3, and (b) polypeptides which comprise an amino acid sequence sharing an identity of 80% or more with the amino acid sequence of any of the polypeptides in (a) and which are responsive to 1,5-octadien-3-ol into contact with 1,5-octadien-3-ol to measure the response of the olfactory receptor polypeptide to 1,5-octadien-3-ol;

(ii) mixing a test substance with 1,5-octadien-3-ol to measure the response of the olfactory receptor polypeptide used in step (i); and (iii) comparing the results measured in steps (i) and (ii) to select a test substance causing a reduction in the response as a candidate substance for 1,5-octadien-3-ol odor-suppressing materials.

The screening method for 1,5-octadien-3-ol odor-suppressing materials according to the present invention is configured such that candidate substances for 1,5-octadien-3-ol odor-suppressing materials are selected from among test substances on the basis of the responsiveness of each test substance to an olfactory receptor polypeptide selected from the group consisting of OR2C1, OR4Q3, and polypeptides which comprise amino acid sequences sharing an identity of 80% or more with the amino acid sequences of these polypeptides and which are responsive to offensive odor-causing substances.

In the screening method for 1,5-octadien-3-ol odor-suppressing materials according to the present invention, the term "test substance" is not limited in any way, but it refers to a subject to be tested for its suppressive effect on a 1,5-octadien-3-ol odor and is intended to mean a compound, a composition or a mixture. Likewise, the term "1,5-octadien-3-ol odor-suppressing material" is not limited in any way, but it is intended to mean a compound, a composition or a mixture, which is capable of suppressing a 1,5-octadien-3-ol odor. Moreover, the term "1,5-octadien-3-ol odor" is intended to mean an odor originating from 1,5-octadien-3-ol, as exemplified by a mushroom odor, an iron rust odor, an underarm odor, off-flavors, etc. An explanation will be given below of each step.

<Step (i)>

In step (i), an olfactory receptor polypeptide selected from the group consisting of OR2C1, OR4Q3, and polypeptides which comprise an amino acid sequence sharing an identity of 80% or more with the amino acid sequence of any of these polypeptides and which are responsive to 1,5-octadien-3-ol is brought into contact with 1,5-octadien-3-ol to measure the response of the olfactory receptor polypeptide to 1,5-octadien-3-ol.

The olfactory receptor polypeptide to be used for this purpose is an olfactory receptor polypeptide selected from the group consisting of OR2C1, OR4Q3, and polypeptides which comprise an amino acid sequence sharing an identity of 80% or more with the amino acid sequence of any of these polypeptides and which are responsive to 1,5-octadien-3-ol.

OR2C1 has been registered in GenBank under NM_012368, and is a polypeptide consisting of an amino acid sequence (SEQ ID NO: 2) encoded by DNA at positions 53 to 991 of the nucleotide sequence shown in SEQ ID NO: 1.

OR4Q3 has been registered in GenBank under NM_172194, and is a polypeptide consisting of an amino acid sequence (SEQ ID NO: 4) encoded by DNA having the nucleotide sequence shown in SEQ ID NO: 3.

Since these polypeptides strongly and selectively respond to 1,5-octadien-3-ol, the screening method using OR2C1 and/or OR4Q3 can be expected to contribute to the development of 1,5-octadien-3-ol odor-suppressing materials.

As an olfactory receptor, it is also possible to use an olfactory receptor polypeptide selected from the group consisting of polypeptides which comprise an amino acid sequence sharing an identity of 80% or more, preferably 85% or more, more preferably 90% or more, even more preferably 95% or more, and particularly preferably 98% or more with the amino acid sequence possessed by any of these polypeptides (i.e., SEQ ID NO: 2 or 4) and which are responsive to 1,5-octadien-3-ol.

Such olfactory receptor polypeptides may be used alone, or two or more of them may be used in combination.

In the present invention, there is no particular limitation on how to contact an olfactory receptor polypeptide with 1,5-octadien-3-ol to measure the response of the olfactory receptor polypeptide to 1,5-octadien-3-ol. For example, the response of the olfactory receptor polypeptide may be measured by being contacted with 1,5-octadien-3-ol on cells isolated from a living body expressing the olfactory receptor polypeptide, or alternatively, the response of the olfactory receptor polypeptide may be measured by being contacted with 1,5-octadien-3-ol on cells genetically engineered to artificially express the olfactory receptor polypeptide. The time required to contact the olfactory receptor polypeptide with 1,5-octadien-3-ol is not determined exactly because it also depends on the concentration of 1,5-octadien-3-ol and the method used for measurement. However, the response may be measured immediately after their contact, and the time required for their contact is usually 0 to 4 hours, and preferably 2 to 4 hours. The same goes for when the olfactory receptor polypeptide is contacted with 1,5-octadien-3-ol in admixture with a test substance.

Cells genetically engineered to artificially express the olfactory receptor polypeptide may be prepared when cells are transformed with a vector carrying a gene encoding the olfactory receptor polypeptide.

In a preferred aspect of the present invention, the N-terminal 20 amino acid residues of bovine rhodopsin may be integrated together with the olfactory receptor polypeptide. Upon integration of the N-terminal 20 amino acid residues of bovine rhodopsin, cell membrane expression of the olfactory receptor polypeptide may be facilitated.

Bovine rhodopsin has been registered in GenBank under NM 001014890. Bovine rhodopsin is a polypeptide consisting of an amino acid sequence (SEQ ID NO: 6) encoded by DNA at positions 1 to 1047 of the nucleotide sequence shown in SEQ ID NO: 5.

Moreover, instead of bovine rhodopsin, it is also possible to use a polypeptide which comprises an amino acid sequence sharing an identity of 80% or more, preferably 85% or more, more preferably 90% or more, even more preferably 95% or more, and particularly preferably 98% or more with the amino acid sequence shown in SEQ ID NO: 6 and which is capable of facilitating cell membrane expression of the olfactory receptor polypeptide.

It should be noted that amino acid residues of not only bovine rhodopsin but also any other polypeptides may be used as long as they can facilitate cell membrane expression of the olfactory receptor polypeptide.

There is no particular limitation on how to measure the response of the olfactory receptor polypeptide, and any technique used in the art may be used for this purpose. For example, it is known that once an odorous compound has bound to an olfactory receptor polypeptide, G protein in cells will be activated and this G protein will in turn activate adenylate cyclase to convert ATP into cyclic AMP (cAMP), thereby increasing the intracellular level of cAMP. Thus, the response of the olfactory receptor polypeptide can be measured when the level of cAMP is measured. The level of cAMP may be measured using ELISA techniques, reporter gene assay techniques, etc. Above all, it is preferred that the response of the olfactory receptor polypeptide is measured by reporter gene assay techniques using a luminophore (e.g., luciferase).

According to one embodiment of the present invention, the response of the olfactory receptor polypeptide may be evaluated on the basis of the fold increase value determined by dividing the results measured in the presence of 1,5-octadien-3-ol by the results measured in the absence of 1,5-octadien-3-ol. For example, when the response of the olfactory receptor polypeptide is measured by reporter gene assay techniques using a luminophore (e.g., luciferase), evaluation can be made using 1,5-octadien-3-ol at a concentration which gives a fold increase value of preferably 2 or more, more preferably 4 or more, and even more preferably 10 or more.

<Step (ii)>

In step (ii), a test substance is mixed with 1,5-octadien-3-ol to measure the response of the olfactory receptor used in step (i).

The response of the olfactory receptor polypeptide may be measured in the same manner as shown in step (i), except that 1,5-octadien-3-ol is mixed with the test substance and contacted with the olfactory receptor polypeptide. For example, the response of the olfactory receptor polypeptide may be measured on cells isolated from a living body expressing the olfactory receptor polypeptide, or alternatively, the response of the olfactory receptor polypeptide may be measured on cells genetically engineered to artificially express the olfactory receptor polypeptide. For proper comparison of the results measured in steps (i) and (ii), the measurement conditions in steps (i) and (ii) are preferably the same, except for the presence or absence of the test substance.

<Step (iii)>

In step (iii), the results measured in steps (i) and (ii) are compared with each other to select a test substance causing a reduction in the response as a candidate substance for 1,5-octadien-3-ol odor-suppressing materials.

In the present invention, when a reduction in the response is observed as a result of comparing the results measured in steps (i) and (ii), the test substance used in step (ii) can be evaluated as a candidate substance for 1,5-octadien-3-ol odor-suppressing materials.

In such a way as described above, test substances can be screened to select candidate substances for 1,5-octadien-3-ol odor-suppressing materials. According to the present invention, it is possible to select candidate substances for 1,5-octadien-3-ol odor-suppressing materials from among many test substances, without causing any problems such as olfactory fatigue and variations among individuals associated with sensory testing by means of the human olfactory sense.

The selected substances can be used as candidate substances for 1,5-octadien-3-ol odor-suppressing materials. If necessary, the selected substances may be subjected to modifications or the like to thereby develop novel compounds having the most suitable scent. Further, the selected substances may be blended with other fragrance or flavor materials to thereby develop fragrance or flavor materials capable of suppressing the 1,5-octadien-3-ol odor and also having the most suitable scent. The screening method of the present invention can be used to contribute to the development of new fragrance or flavor materials serving as 1,5-octadien-3-ol odor-suppressing materials.

5. Offensive Odor-Suppressing Composition

The screening method of the present invention can be used to select an offensive odor-suppressing material suitable for each offensive odor-causing substance, and such an offensive odor-suppressing material can be used as an active ingredient to give an offensive odor-suppressing composition for each intended purpose.

In one embodiment of the present invention, the offensive odor-suppressing composition contains at least one compound selected from the following group (A) as an active ingredient.

The group (A) includes 2-methyl-4-(2,2,3-trimethylcyclopent-3-enyl)but-2-en-1-ol (Hindinol®), 1-(2,2,6-trimethylcyclohexyl)hexan-3-ol (Dextramber®), 1,4-dioxacycloheptadecane-5,17-dione, eucalyptus oil, patchouli oil, vetiver oil and so on. The amount of the group (A) in the offensive odor-suppressing composition of the present invention is not limited strictly, and is preferably 0.0001% by weight or more, more preferably 0.001% to 20% by weight, and even more preferably 0.01% to 10% by weight.

The offensive odor-suppressing composition containing the above group (A) particularly can suppress age-related body odors and/or underarm odors which are offensive odors composed of at least one selected from the group consisting of a 1-octen-3-one odor and a 1,5-octadien-3-one odor. Moreover, the offensive odor-suppressing composition containing the above group (A) can suppress age-related body odors and/or underarm odors which are offensive odors composed of at least one selected from the group consisting of a trans-2-nonenal odor and a trans-2-octenal odor.

The offensive odor-suppressing composition of the present invention may comprise known fragrances or commonly used additives as described below within the range that will not impair the effect of the present invention, i.e., within the quantitative and qualitative range that can overcome the olfactory offensiveness associated with the age-related body odors and/or underarm odors.

Examples of known fragrances include hydrocarbons (e.g., α-pinene, limonene, cedrene); aliphatic saturated or unsaturated alcohols (e.g., 1-octen-3-ol, nonanol); saturated or unsaturated linear terpene alcohols (e.g., myrcenol, tetrahydrolinalool, nerol); cyclic terpene alcohols (e.g., α-terpineol, bornyl methoxy cyclohexanol); sesquiterpene alcohols (e.g., farnesol); aromatic alcohols (e.g., γ-phenylpropyl alcohol, dimethylbenzylcarbinol); aliphatic aldehydes, terpene-based aldehydes, aromatic aldehydes, aliphatic ketones (e.g., Iso E Super (7-acetyl-1,2,3,4,5,6,7,8-octahydro-1,1,6, 7-tetramethylnaphthalene)); terpene-based cyclic ketones, cyclic ketones, aliphatic esters, acetic acid esters, propionic acid esters, butyric acid esters, benzoic acid esters, phenylacetic acid esters, salicylic acid esters, anthranilic acid esters and so on. The amount of these known fragrances in the offensive odor-suppressing composition of the present invention may be selected as appropriate depending on the type of fragrance to be used and/or the intended purpose, and is not limited in any way.

The offensive odor-suppressing composition of the present invention can be incorporated into various types of products, and perfumery and cosmetics are also one of the preferred products. The offensive odor-suppressing composition of the present invention mentioned above may be incorporated into, e.g., perfumery and cosmetics together with commonly used additives, depending on its form or its dosage form.

Examples of commonly used additives include known UV absorbers; algefacients (e.g., menthol, methyl salicylate); skin stimulants (e.g., capsicum tincture, nonylic vanillylamide), and so on. The amount of these commonly used additives is not limited in any way, but it is within the range of approximately 0.005% to 5.0% by weight relative to the total weight of the offensive odor-suppressing composition of the present invention.

Moreover, the offensive odor-suppressing composition of the present invention may be incorporated in an amount commonly used in the art into, for example, fragrance products, perfumery and cosmetics, basic cosmetics, make-up cosmetics, hair cosmetics, sun care cosmetics, medicated cosmetics, hair care products, soaps, body cleansers, bath preparations, fabric detergents, soft-finishing agents, detergents, kitchen detergents, bleaching agents, aerosols, air fresheners, repellents and/or sundry goods to enhance their commercial value.

Examples of fragrance products include perfume, eau de parfum, eau de toilette, eau de cologne, and so on; examples of basic cosmetics include face wash cream, vanishing cream, cleansing cream, cold cream, massage cream, skin milk, lotion, essence, facial pack, make-up remover, and so on; examples of make-up cosmetics include foundation, lipstick, lip pomade, and so on; examples of hair cosmetics include hair tonic, hair liquid, hair spray, and so on; examples of sun care cosmetics include suntan products, sunscreen products, and so on; and examples of medicated cosmetics include antiperspirant, after shaving lotion and gel, permanent waving agent, medicated soap, medicated shampoo, medicated skin cosmetics, and so on.

Examples of hair care products include shampoo, conditioner, two-in-one shampoo, hair conditioner, hair treatment, hair pack, and so on; examples of soaps include toilet soap, bath soap, and so on; examples of body cleansers include body wash, body shampoo, hand wash, and so on; and examples of bath preparations include bath additives (e.g., bath salt, bath tablet, bath liquid), foam bath (e.g., bubble bath), bath oil (e.g., bath perfume, bath capsule), milk bath, bath gel, bath cube and so on.

Examples of fabric detergents include heavy fabric detergent, light fabric detergent, liquid detergent, laundry soap, concentrated detergent, powdered soap, and so on; examples of soft-finishing agents include softener, furniture care, and so on; examples of detergents include cleanser, household cleaner, toilet detergent, bath detergent, glass cleaner, mold remover, drain detergent, and so on; examples of kitchen detergents include kitchen soap, kitchen synthetic soap, dish detergent, and so on; examples of bleaching agents include oxidizing bleaching agents (e.g., chlorine-based bleaching agent, oxygen-based bleaching agent), reducing bleaching agents (e.g., sulfur-based bleaching agent), optical bleaching agents, and so on; examples of aerosols include those of spray type, powder spray, and so on; examples of air fresheners include those of solid type, gel type or liquid type, and so on; and examples of sundry goods include those of various forms such as tissue paper, toilet paper, and so on.

When the offensive odor-suppressing composition of the present invention is used in the above products, the composition may be used as such or converted into any form depending on the intended purpose, as exemplified by a liquid form dissolved in an alcohol or a polyhydric alcohol (e.g., propylene glycol, glycerin); a solubilized or dispersed form solubilized or dispersed with a surfactant (e.g., a nonionic surfactant, an anionic surfactant, a cationic surfactant, an amphoteric surfactant); or a microcapsule form obtained by treatment with an encapsulating agent, etc.

Further, the above offensive odor-suppressing composition may be used in a stable and sustained release form by being included in an inclusion agent such as cyclodextrin. These forms are suitable as final product forms (e.g., liquid, solid, powder, gel, mist and aerosol forms) and may be selected as appropriate.

Further, the offensive odor-suppressing composition of the present invention does not serve as an odorant by itself, but is used by being incorporated into a profragrance which has the ability to release the above offensive odor-suppressing composition under use/application conditions. In this case, the amount of the offensive odor-suppressing composition of the present invention is not limited in any way, but it is within the range of approximately 0.001% to 20.0% by weight relative to the total weight of the product.

6. Flavor Composition

The flavor composition of the present invention contains, as an active ingredient, a flavor component suppressing the intensity of response to at least one olfactory receptor polypeptide selected from the group consisting of OR2C, OR4Q3, and polypeptides which comprise an amino acid sequence sharing an identity of at least 80% with the amino acid sequence of any of these polypeptides and which are responsive to one or more offensive odor-causing substances selected from the group consisting of 1-octen-3-one, 1,5-octadien-3-one, 1-octen-3-ol and 1,5-octadien-3-ol.

The flavor composition of the present invention may comprise known flavorings or commonly used additives as described below within the range that will not impair the effect of the present invention, i.e., within the quantitative and qualitative range that can reduce off-flavors from food and beverage products. The flavor composition of the present invention may also be incorporated into a composition for oral use within the range that will not impair the effect of the present invention.

Other components which may be incorporated into the flavor composition of the present invention include various synthetic flavorings, natural flavorings, natural essential oils, plant extracts and so on, as exemplified by natural essential oils, natural fragrances or flavorings, synthetic fragrances or flavorings and so on as appear in "Japanese Patent Office Bulletin, Collection of Well-known Prior Arts (Flavorings and Fragrances) Part II Food Flavors, P88 to 131, published on Jan. 14, 2000."

The flavor composition of the present invention may optionally contain, for example, a solvent (e.g., water, ethanol) and/or a fixative (e.g., ethylene glycol, propylene glycol, dipropylene glycol, hexylene glycol, glycerin, triethyl citrate, medium chain fatty acid triglyceride, medium chain fatty acid diglyceride), which are commonly used.

The food and beverage products intended in the present invention include:

beverages such as fruit drinks, fruit liquors, milk beverages, carbonated beverages, soft drinks, and drinkable preparations; tea beverages or palatable beverages such as green tea, oolong tea, black tea, persimmon leaf tea, chamomile tea, kumazasa (*Sasa albo-marginata*) tea, mulberry leaf tea, dokudami (*Houttuynia cordata*) tea, pu-erh tea, mate tea, rooibos tea, gymnema tea, guava tea, coffee, and cocoa; soups such as Japanese soups, western soups, and Chinese soups; various instant beverages, etc.; and frozen desserts such as ice creams, sorbets, and ice lollies; desserts such as jellies and puddings; western confectionery such as cakes, cookies, chocolates, and chewing gums; Japanese confectionery such as manju (sweet bean paste buns), yokan (sweet bean paste jelly), and uiro (sweet rice jelly); jams; candies; bakery products; flavorings and seasonings; various instant foods; various junk foods, etc.

The above composition for oral use includes dentifrices, oral washes, mouth washes, troches, chewing gums, etc.

EXAMPLES

The present invention will be further described in more detail below by way of the following illustrative examples, although the present invention is not limited to these examples.

Example 1

Measurement of Olfactory Receptor Response to 1-Octen-3-One (1) Cloning of Olfactory Receptor Genes Human olfactory receptor genes were obtained by PCR cloning with Human Genomic DNA: Female (Promega) on the basis of their sequence information registered in Gen-Bank. Into pME18S vectors, the N-terminal 20 amino acid residues of bovine rhodopsin were integrated and the result-ing human olfactory receptor genes were integrated respectively downstream thereof to obtain human olfactory receptor gene expression vectors.

(2) Expression of Olfactory Receptor Genes in HEK293T Cells

Each human olfactory receptor gene expression vector (0.05 μg), RTP1S vector (0.01 μg), firefly luciferase vector pGL4.29 containing a cAMP response element promoter (Promega, 0.01 μg) and *Renilla* luciferase vector pGL4.74 containing a thymidine kinase promoter (Promega, 0.005 μg) were dissolved in 10 μL of Opti-MEMI (gibco) to give a gene solution (for one well). HEK293T cells were seeded in 100 μL volumes into 96-well plates (Biocoat, Corning) at a cell density reaching confluence after 24 hours, and the gene solutions were added to the respective wells to cause gene transfer into the cells by lipofection techniques in accordance with the usage of Lipofectamine 3000, followed by culture at 37° C. under a 5% carbon dioxide atmosphere for 24 hours.

(3) Luciferase Reporter Gene Assay

After removal of the culture solutions, an odorous substance serving as an analyte, which had been prepared at a given concentration with CD293 (gibco) medium (supplemented with 20 μM L-glutamine), was added in 50 μL volumes to stimulate the cells for 3 hours, followed by luciferase activity measurement in accordance with the usage of a Dual-Luciferase Reporter Assay System (Promega). The response intensity of each olfactory receptor polypeptide was expressed as a fold increase value, which was determined by dividing the luciferase activity generated upon stimulation with the odorous substance by the luciferase activity generated in a test system not containing the odorous substance.

Figure 2:
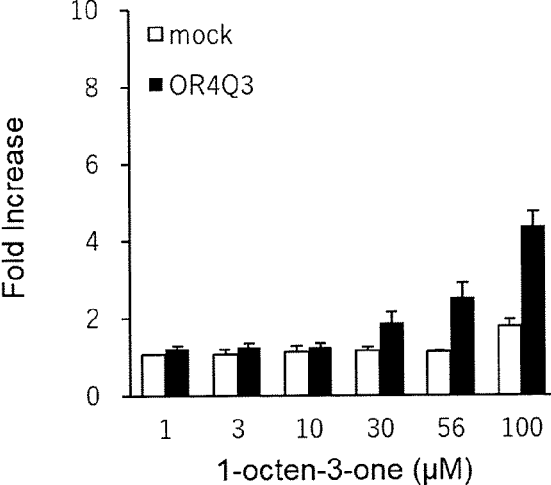
FIG. 2 shows the results measured for the response of olfactory receptor OR4Q3 to 1-octen-3-one.

(4) Identification of Olfactory Receptor Polypeptides Responding to 1-Octen-3-One The cells engineered to express human olfactory receptors OR2C1 and OR4Q3 were used to measure the response of these receptors to various concentrations of 1-octen-3-one by the luciferase reporter gene assay. The results obtained are shown in FIGS. 1 and 2, respectively. These two receptors were both found to respond to 1-octen-3-one in a concentration-dependent manner. In contrast, no response was observed in a Mock test using cells not engineered to express the olfactory receptors. Namely, OR2C1 and OR4Q3 were shown to specifically respond to 1-octen-3-one.

Example 2

Measurement of Olfactory Receptor Response to 1,5-Octadien-3-One

Figure 3:
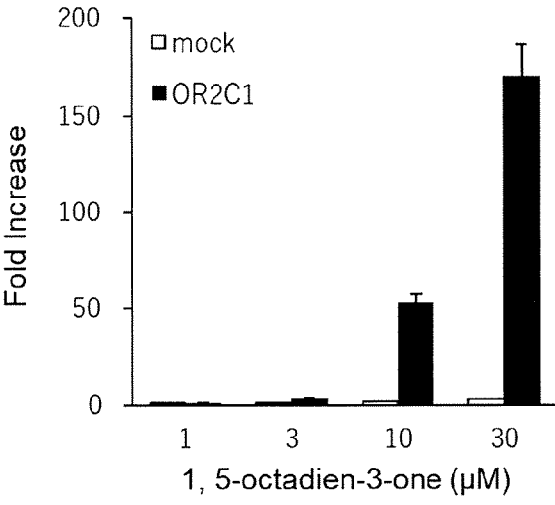
FIG. 3 shows the results measured for the response of olfactory receptor OR2C1 to 1,5-octadien-3-one.
Figure 4:
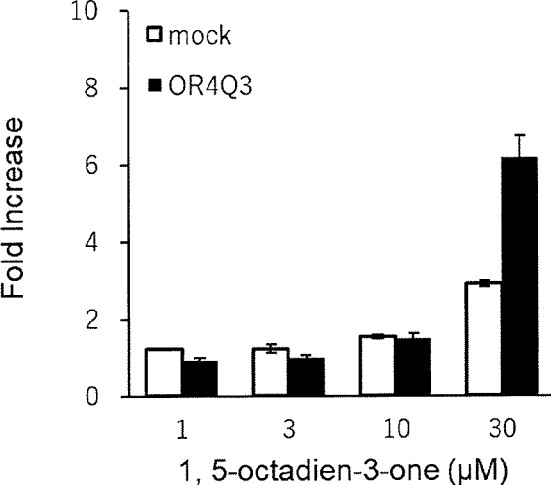
FIG. 4 shows the results measured for the response of olfactory receptor OR4Q3 to 1,5-octadien-3-one.

According to the same procedure as shown in Example 1, the cells engineered to express human olfactory receptors OR2C1 and OR4Q3 were used to measure the response of these receptors to various concentrations of 1,5-octadien-3-one by the luciferase reporter gene assay. The results obtained are shown in FIGS. 3 and 4, respectively. These two receptors were both found to respond to 1,5-octadien-3-one in a concentration-dependent manner. In contrast, no response was observed in a Mock test. Namely, OR2C1 and OR4Q3 were shown to specifically respond to 1,5-octadien-3-one.

Example 3

Measurement of Olfactory Receptor Response to 1-Octen-3-Ol

Figure 5:
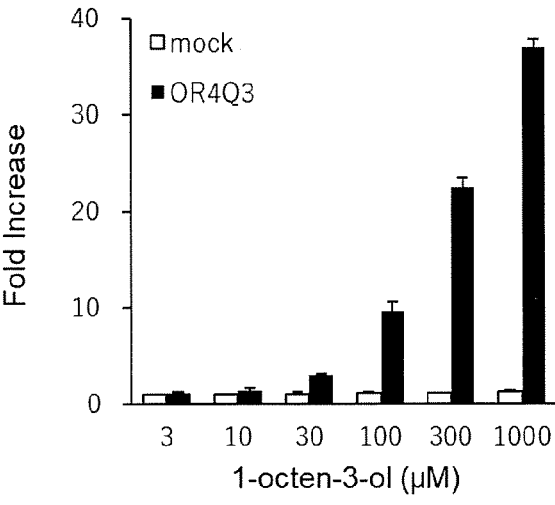
FIG. 5 shows the results measured for the response of olfactory receptor OR4Q3 to 1-octen-3-ol.

According to the same procedure as shown in Example 1, the cells engineered to express human olfactory receptor OR4Q3 were used to measure the response of this receptor to various concentrations of 1-octen-3-ol by the luciferase reporter gene assay. The results obtained are shown in FIG. 5. OR4Q3 was found to respond to 1-octen-3-ol in a concentration-dependent manner. In contrast, no response was observed in a Mock test. Namely, OR4Q3 was shown to specifically respond to 1-octen-3-ol.

Example 4

Measurement of Olfactory Receptor Response to 1,5-Octadien-3-ol

Figure 6:
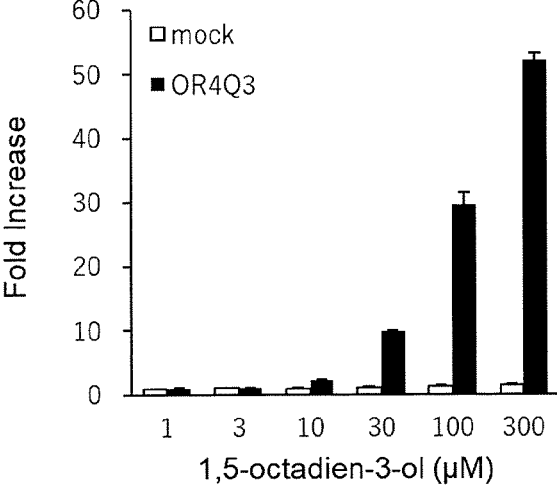
FIG. 6 shows the results measured for the response of olfactory receptor OR4Q3 to 1,5-octadien-3-ol.

According to the same procedure as shown in Example 1, the cells engineered to express human olfactory receptor OR4Q3 were used to measure the response of this receptor to various concentrations of 1,5-octadien-3-ol by the luciferase reporter gene assay. The results obtained are shown in FIG. 6. OR4Q3 was found to respond to 1,5-octadien-3-ol in a concentration-dependent manner. In contrast, no response was observed in a Mock test. Namely, OR4Q3 was shown to specifically respond to 1,5-octadien-3-ol.

Example 5

Figure 7:
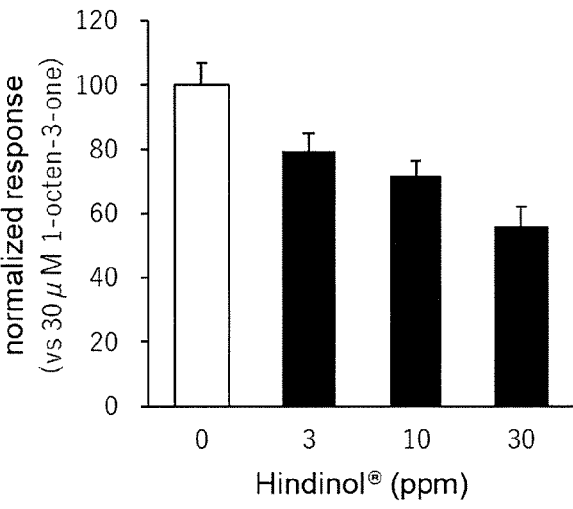
FIG. 7 shows the results obtained for the suppressive effect induced by addition of 2-methyl-4-(2,2,3-trimethyl-cyclopent-3-enyl)but-2-en-1-ol (Hindinol®) on the response of olfactory receptor OR2C1 to 1-octen-3-one.
Figure 8:
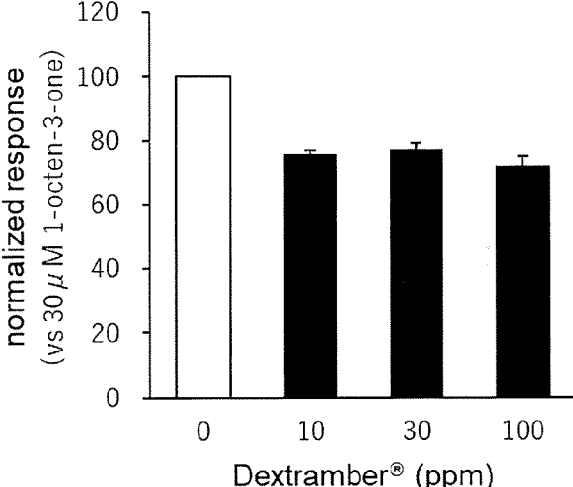
FIG. 8 shows the results obtained for the suppressive effect induced by addition of 1-(2,2,6-trimethylcyclohexyl) hexan-3-ol (Dextramber®) on the response of olfactory receptor OR2C1 to 1-octen-3-one.

Evaluation of Offensive Odor-Suppressing Materials for their Suppressive Effect on the Response of OR2C1 to 1-Octen-3-One Odor According to the same procedure as shown in Example 1, offensive odor-suppressing materials 2-methyl-4-(2,2,3-trimethylcyclopent-3-enyl)but-2-en-1-ol (also known as 2-methyl-4-(2,2,3-trimethyl-3-cyclopentenyl)-2-buten-1-ol) (Hindinol®) and 1-(2,2,6-trimethylcyclohexyl)hexan-3-ol (Dextramber®) were each mixed at various concentrations with 30 µM 1-octen-3-one, and the cells engineered to express OR2C1 were used to measure the response of this receptor to 1-octen-3-one. The ratio of the fold increase value obtained in the test using the offensive odor-suppressing materials was determined assuming that the fold increase value obtained in the test without mixing the offensive odor-suppressing materials was set to 100. The results obtained are shown in FIGS. 7 and 8, respectively. 2-Methyl-4-(2,2,3-trimethylcyclopent-3-enyl)but-2-en-1-ol and 1-(2,2,6-trimethylcyclohexyl)hexan-3-ol both showed the effect of reducing the response of OR2C1 to 1-octen-3-one in a concentration-dependent manner.

Example 6

Figure 9:
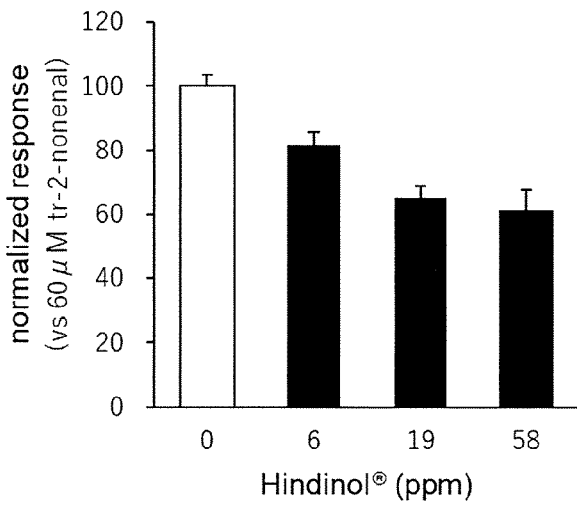
FIG. 9 shows the results obtained for the suppressive effect induced by addition of 2-methyl-4-(2,2,3-trimethyl-cyclopent-3-enyl)but-2-en-1-ol (Hindinol©) on the response of olfactory receptor OR2C1 to trans-2-nonenal.
Figure 10:
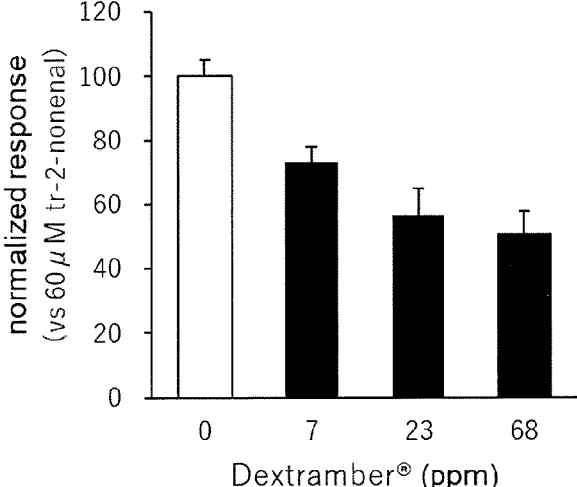
FIG. 10 shows the results obtained for the suppressive effect induced by addition of 1-(2,2,6-trimethylcyclohexyl) hexan-3-ol (Dextramber®) on the response of olfactory receptor OR2C1 to trans-2-nonenal.

Evaluation of Offensive Odor-Suppressing Materials for their Suppressive Effect on the Response of OR2C1 to Trans-2-Nonenal Odor According to the same procedure as shown in Example 5, offensive odor-suppressing materials 2-methyl-4-(2,2,3-trimethylcyclopent-3-enyl)but-2-en-1-ol (Hindinol®) and 1-(2,2,6-trimethylcyclohexyl)hexan-3-ol (Dextramber®) were each mixed at various concentrations with 60 µM trans-2-nonenal, and the cells engineered to express OR2C1 were used to measure the response of this receptor to trans-2-nonenal. The results obtained are shown in FIGS. 9 and 10, respectively. 2-Methyl-4-(2,2,3-trimethylcyclopent-3-enyl)but-2-en-1-ol and 1-(2,2,6-trimethylcyclohexyl) hexan-3-ol both showed the effect of reducing the response of OR2C1 to trans-2-nonenal in a concentration-dependent manner.

INDUSTRIAL APPLICABILITY

By using the screening method of the present invention, candidate substances for materials suppressing a 1-octen-3-one odor, a 1,5-octadien-3-one odor, a 1-octen-3-ol odor and a 1,5-octadien-3-ol odor can be selected respectively from among many test substances. The screening method of the present invention can be expected to contribute to the development of 1-octen-3-one odor-suppressing materials, 1,5-octadien-3-one odor-suppressing materials, 1-octen-3-ol odor-suppressing materials and 1,5-octadien-3-ol odor-suppressing materials. Moreover, the offensive odor-suppressing composition of the present invention can be expected to contribute to reduction in the offensiveness of age-related body odors and/or underarm odors.

The invention claimed is:

1. A screening method for materials suppressing one or more offensive odors selected from the group consisting of a 1-octen-3-one odor, a 1,5-octadien-3-one odor, and a 1,5-octadien-3-ol odor, the method comprising the following steps:

adding a test substance and one or more offensive odor-causing substances selected from the group consisting of 1-octen-3-one, 1,5-octadien-3-one, and 1,5-octadien-3-ol to at least one olfactory receptor polypeptide selected from the group consisting of OR2C1 having an amino acid sequence of SEQ ID NO: 2 and OR4Q3 having an amino acid sequence of SEQ ID NO: 4;

measuring the response of the olfactory receptor polypeptide to the one or more offensive odor-causing substances selected from the group consisting of 1-octen-3-one, 1,5-octadien-3-one, and 1,5-octadien-3-ol; and identifying a test substance that suppresses the response of the olfactory receptor polypeptide on the basis of the measured response.

2. The method according to claim 1, wherein the offensive odors are one or more selected from the group consisting of a 1-octen-3-one odor and a 1,5-octadien-3-one odor.

3. The method according to claim 1, wherein the response of the olfactory receptor polypeptide is measured on cells isolated from a living body expressing the olfactory receptor polypeptide or on cells genetically engineered to artificially express the olfactory receptor polypeptide.

4. The method according to claim 1, wherein the response of the olfactory receptor polypeptide is measured by reporter gene assay.

\*  \*  \*  \*  \*